(12) United States Patent
Caputo et al.

(10) Patent No.: US 10,643,743 B2
(45) Date of Patent: May 5, 2020

(54) WIRELESS INVENTORY MANAGEMENT SYSTEM

(71) Applicant: MEPS Real-Time, Inc., Carlsbad, CA (US)

(72) Inventors: Jimmy C. Caputo, San Diego, CA (US); Shariq Hussain, Vista, CA (US); Jeffrey Shamblin, San Marcos, CA (US)

(73) Assignee: MEPS Real-Time, Inc., Carlsbad, CA (US)

( * ) Notice: Subject to any disclaimer, the term of this patent is extended or adjusted under 35 U.S.C. 154(b) by 0 days.

(21) Appl. No.: 16/518,947

(22) Filed: Jul. 22, 2019

(65) Prior Publication Data
US 2020/0013494 A1 Jan. 9, 2020

Related U.S. Application Data

(63) Continuation of application No. 15/413,278, filed on Jan. 23, 2017, now Pat. No. 10,360,350, which is a
(Continued)

(51) Int. Cl.
*G16H 20/13* (2018.01)
*G06K 7/10* (2006.01)
(Continued)

(52) U.S. Cl.
CPC ......... *G16H 20/13* (2018.01); *G06K 7/10178* (2013.01); *G06K 7/10366* (2013.01);
(Continued)

(58) Field of Classification Search
CPC ........ G16H 20/13; G16H 10/60; G16H 50/70; G16H 70/20; G16H 50/00; G16H 70/00; G06Q 10/087; G06Q 50/22; G06Q 50/24; G06Q 30/00; G06K 7/10178; G06K 19/07749; G06K 7/10366; G06K 7/0008; G06K 17/00; G16B 50/00; G16Z 99/00;
(Continued)

(56) References Cited

U.S. PATENT DOCUMENTS 5,977,875 A 11/1999 Lin
6,768,472 B2 7/2004 Alexopoulos et al.
(Continued)

*Primary Examiner* — Ryan W Sherwin
(74) *Attorney, Agent, or Firm* — Thomas A. Runk; Brooks Kushman P.C.

(57) ABSTRACT

An inventory management system for wirelessly taking inventories of medical trays comprises an easily assemblable and disassemblable enclosure comprising interconnected electrically conductive walls to form a Faraday cage. The interior space defined by the walls is large enough to accept the trays. RFID readers are placed within the enclosure directed at the tray to excite and read the RFID tags disposed on the medical articles within the tray. The walls of the enclosure are flexible and one of the walls is rolled up and down to act as an opening to the interior space. A host computer stores the inventory of the tray and compares it against a previous inventory existence for resupply purposes. The host computer also detects expired and recalled medical articles in the tray. If a recalled article is detected, the host computer determines if a substitute article exists.

25 Claims, 20 Drawing Sheets

Related U.S. Application Data continuation of application No. 14/853,944, filed on Sep. 14, 2015, now Pat. No. 9,552,568, which is a continuation of application No. 14/210,287, filed on Mar. 13, 2014, now Pat. No. 9,135,482, which is a continuation-in-part of application No. 13/776,613, filed on Feb. 25, 2013, now Pat. No. 8,686,859, which is a continuation of application No. 12/631,861, filed on Dec. 7, 2009, now Pat. No. 8,384,545.

(60) Provisional application No. 61/780,698, filed on Mar. 13, 2013.

(51) Int. Cl.
    *G06Q 10/08*     (2012.01)
    *G16H 70/20*     (2018.01)
    *G06K 19/077*    (2006.01)
    *G16B 50/00*     (2019.01)
    *G16H 10/60*     (2018.01)
    *G16H 50/70*     (2018.01)
    *G06Q 50/22*     (2018.01)

(52) U.S. Cl.
    CPC ..... *G06K 19/07749* (2013.01); *G06Q 10/087* (2013.01); *G06Q 50/22* (2013.01); *G16B 50/00* (2019.02); *G16H 10/60* (2018.01); *G16H 50/70* (2018.01); *G16H 70/20* (2018.01)

(58) Field of Classification Search
    CPC .... G06F 19/00; G06F 19/326; G06F 19/3462; G06F 19/30; H04Q 9/00; H04Q 2209/47
    See application file for complete search history.

(56) References Cited

U.S. PATENT DOCUMENTS

| | | | |
|---|---|---|---|
| 7,095,326 B2 | 8/2006 | Young et al. | |
| 7,369,919 B2 * | 5/2008 | Vonk | A61J 7/0481 700/236 |
| 7,492,261 B2 | 2/2009 | Cambre et al. | |
| 8,031,124 B2 | 10/2011 | Kato et al. | |
| 8,085,150 B2 | 12/2011 | Oberle | |
| 8,215,549 B2 | 7/2012 | Arpino | |
| 8,313,024 B2 * | 11/2012 | Marino | G06Q 10/08 235/383 |
| 8,384,545 B2 | 2/2013 | Hussain et al. | |
| 8,686,859 B2 | 4/2014 | Hussain et al. | |
| 9,307,756 B2 | 4/2016 | Clement et al. | |
| 9,922,304 B2 | 3/2018 | De Busk et al. | |
| 2005/0088306 A1 | 4/2005 | Andreasson et al. | |
| 2006/0244588 A1 | 11/2006 | Hannah et al. | |
| 2007/0001809 A1 | 1/2007 | Kodukula et al. | |
| 2008/0094214 A1 | 4/2008 | Azevedo et al. | |
| 2009/0128299 A1 | 5/2009 | Kirmeier et al. | |
| 2009/0251293 A1 * | 10/2009 | Azevedo | G07G 1/009 340/10.1 |
| 2010/0265068 A1 | 10/2010 | Brackmann et al. | |
| 2011/0285536 A1 | 11/2011 | Sriharto et al. | |
| 2012/0042808 A1 * | 2/2012 | Allen | A61B 50/10 108/25 |
| 2012/0044054 A1 | 2/2012 | Hussain et al. | |
| 2014/0197954 A1 | 7/2014 | Caputo et al. | |
| 2014/0210596 A1 | 7/2014 | Hussain et al. | |

* cited by examiner

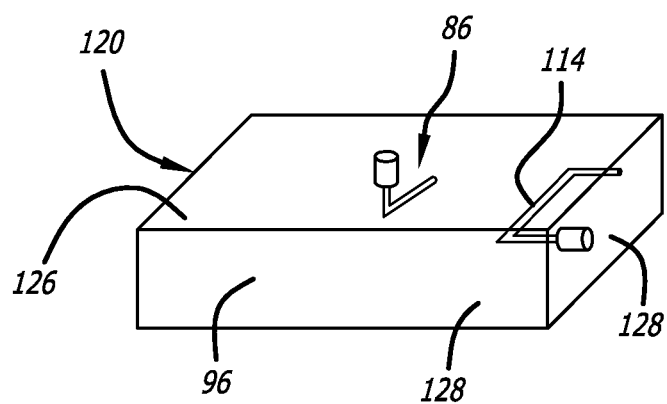
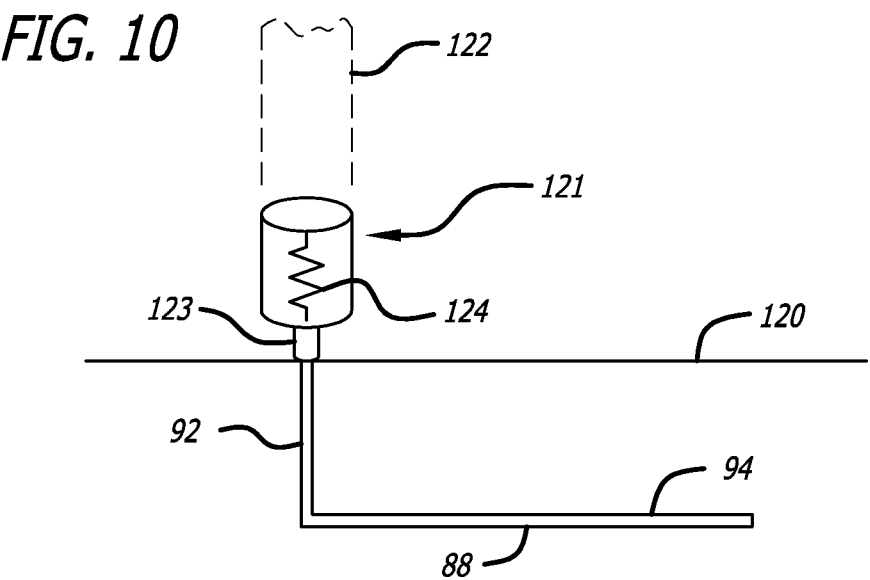

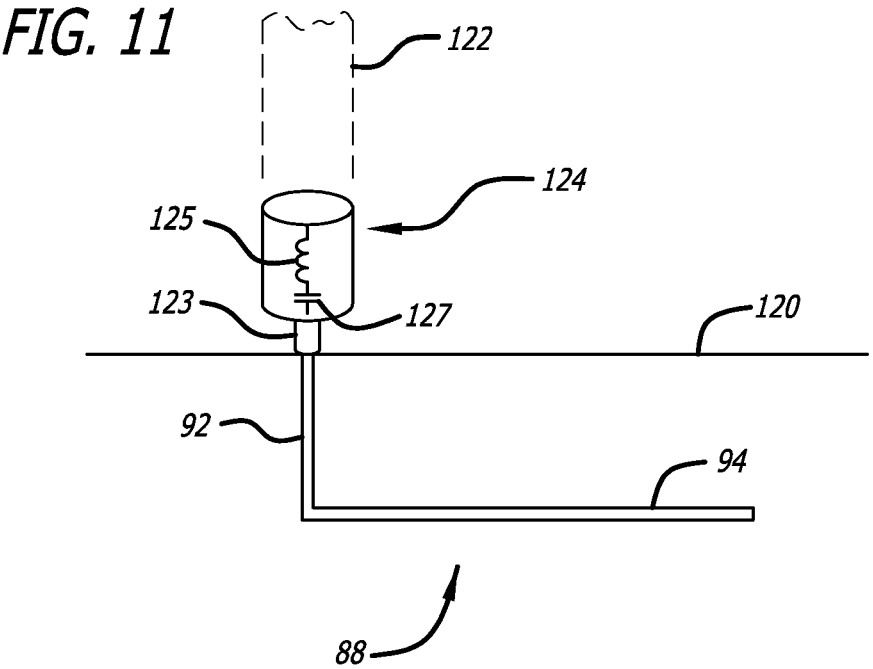
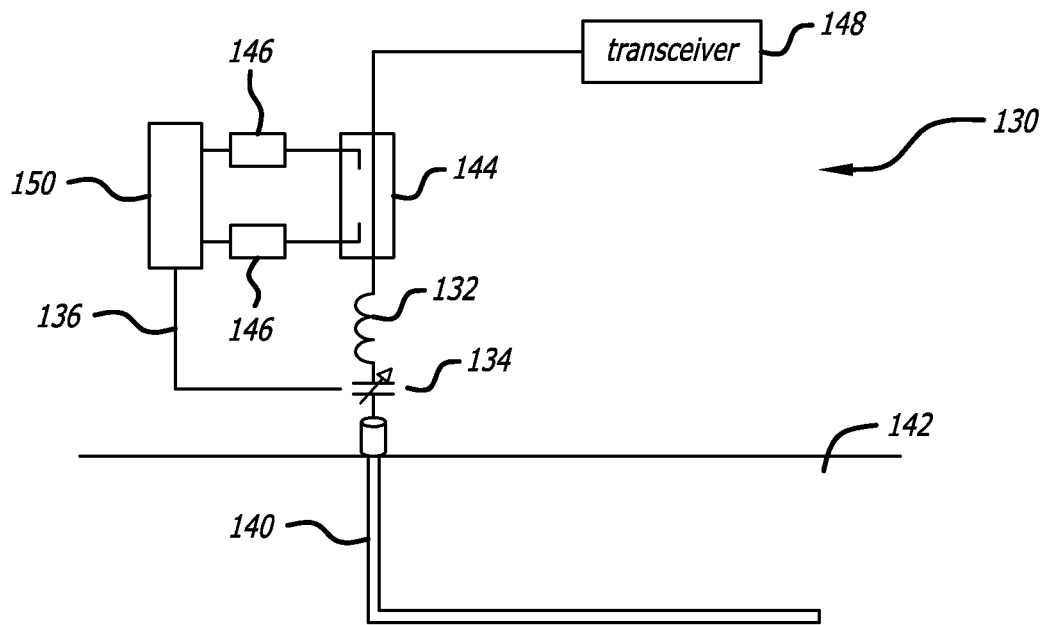

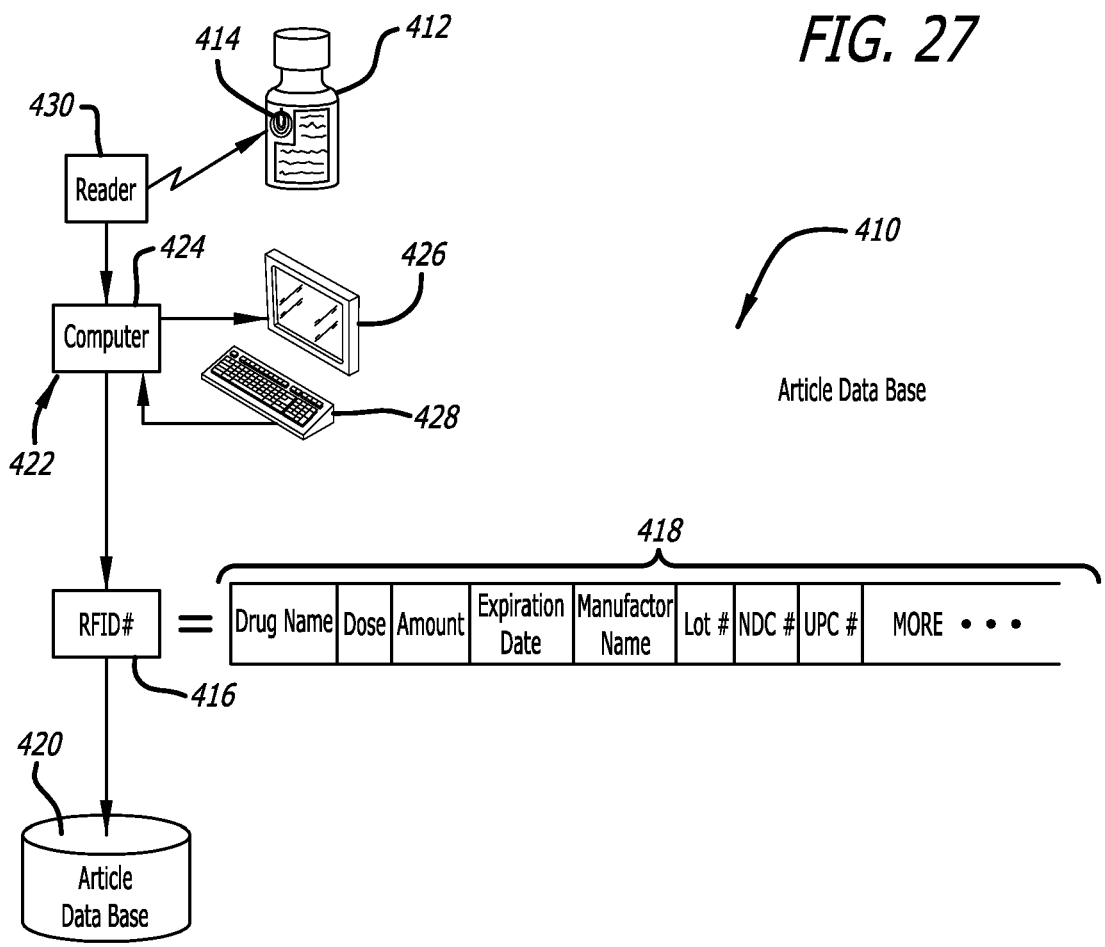
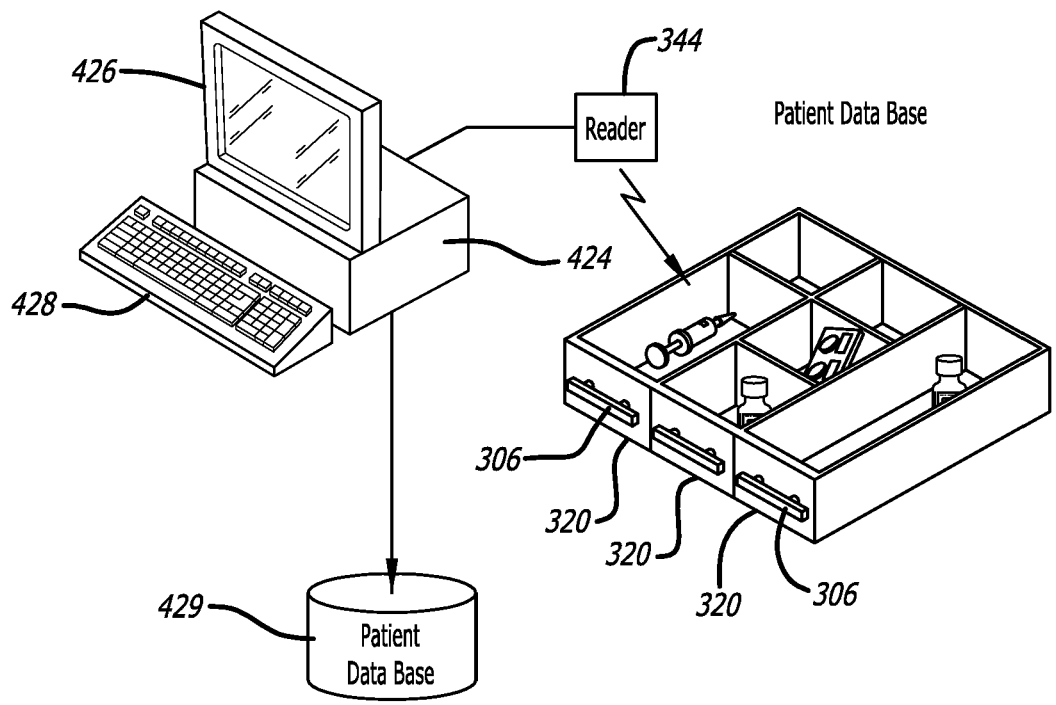
FIG. 27

WIRELESS INVENTORY MANAGEMENT SYSTEM

CROSS-REFERENCES TO RELATED APPLICATIONS

This application is a continuation of U.S. application Ser. No. 15/413,278, filed Jan. 23, 2017, now U.S. Pat. No. 10,360,350, which is a continuation of U.S. application Ser. No. 14/853,944, filed Sep. 14, 2015, now U.S. Pat. No. 9,552,568, which is a continuation of U.S. application Ser. No. 14/210,287, filed Mar. 13, 2014, now U.S. Pat. No. 9,135,482, which is a continuation-in-part of U.S. application Ser. No. 13/776,613 filed Feb. 25, 2013, now U.S. Pat. No. 8,686,859, and which claims the benefit of U.S. Provisional Application No. 61/780,698, filed Mar. 13, 2013, and which is a continuation of U.S. application Ser. No. 12/631,861, filed Dec. 7, 2009, now U.S. Pat. No. 8,384,545, all of which are incorporated herein by reference.

BACKGROUND

The invention relates generally to the field of tracking medical articles in a healthcare setting, and more particularly, to a system and method for managing the inventory of a mobile medical dispensing cart.

There are a number of ways of identifying and tracking articles including visually, optically (bar coding, for example), magnetically, electro-magnetically (RFID), weighing, and others. Where an automatic system for tracking is desired, RFID is a candidate since identification data may be obtained wirelessly. RFID tags have decreased in cost, which has made them even more attractive for such an application.

Radio-frequency identification ("RFID") is the use of electromagnetic energy ("EM energy") to stimulate a responsive device (known as an RFID "tag" or transponder) to identify itself and in some cases, provide additionally stored data. RFID tags typically include a semiconductor device having a memory, circuitry, and one or more conductive traces that form an antenna. Typically, RFID tags act as transponders, providing information stored in the semiconductor device memory in response to an RF interrogation signal received from a reader, also referred to as an interrogator. Some RFID tags include security measures, such as passwords and/or encryption. Many RFID tags also permit information to be written or stored in the semiconductor memory via an RF signal.

RFID tags may be incorporated into or attached to articles to be tracked. In some cases, the tag may be attached to the outside of an article with adhesive, tape, or other means and in other cases, the tag may be inserted within the article, such as being included in the packaging, located within the container of the article, or sewn into a garment. The RFID tags are manufactured with a unique identification number which is typically a simple serial number of a few bytes with a check digit attached. This identification number is incorporated into the tag during manufacture. The user cannot alter this serial/identification number and manufacturers guarantee that each serial number is used only once. This configuration represents the low cost end of the technology in that the RFID tag is read-only and it responds to an interrogation signal only with its identification number. Typically, the tag continuously responds with its identification number. Data transmission to the tag is not possible. These tags are very low cost and are produced in enormous quantities.

Such read-only RFID tags typically are permanently attached to an article to be tracked and, once attached, the serial number of the tag is associated with its host article in a computer data base. For example, a particular type of medicine may be contained in hundreds or thousands of small vials. Upon manufacture, or receipt of the vials at a health care institution, an RFID tag is attached to each vial. Each vial with its permanently attached RFID tag will be checked into the data base of the health care institution upon receipt. The RFID identification number may be associated in the data base with the type of medicine, size of the dose in the vial, and perhaps other information such as the expiration date of the medicine. Thereafter, when the RFID tag of a vial is interrogated and its identification number read, the data base of the health care institution can match that identification number with its stored data about the vial. The contents of the vial can then be determined as well as any other characteristics that have been stored in the data base. This system requires that the institution maintain a comprehensive data base regarding the articles in inventory rather than incorporating such data into an RFID tag.

An object of the tag is to associate it with an article throughout the article's life in a particular facility, such as a manufacturing facility, a transport vehicle, a health care facility, a storage area, or other, so that the article may be located, identified, and tracked, as it is moved. For example, knowing where certain medical articles reside at all times in a health care facility can greatly facilitate locating needed medical supplies when emergencies arise. Similarly, tracking the articles through the facility can assist in generating more efficient dispensing and inventory control systems as well as improving work flow in a facility. Additionally, expiration dates can be monitored and those articles that are older and about to expire can be moved to the front of the line for immediate dispensing. This results in better inventory control and lowered costs.

Other RFID tags are writable and information about the article to which the RFID tag is attached can be programmed into the individual tag. While this can provide a distinct advantage when a facility's computer servers are unavailable, such tags cost more, depending on the size of the memory in the tag. Programming each one of the tags with information contained in the article to which they are attached involves further expense.

RFID tags may be applied to containers or articles to be tracked by the manufacturer, the receiving party, or others. In some cases where a manufacturer applies the tags to the product, the manufacturer will also supply a respective data base file that links the identification number of each of the tags to the contents of each respective article. That manufacturer supplied data base can be distributed to the customer in the form of a file that may easily be imported into the customer's overall data base thereby saving the customer from the expense of creating the data base.

Many RFID tags used today are passive in that they do not have a battery or other autonomous power supply and instead, must rely on the interrogating energy provided by an RFID reader to provide power to activate the tag. Passive RFID tags require an electromagnetic field of energy of a certain frequency range and certain minimum intensity in order to achieve activation of the tag and transmission of its stored data. Another choice is an active RFID tag; however, such tags require an accompanying battery to provide power to activate the tag, thus increasing the expense of the tag and making them undesirable for use in a large number of applications.

Depending on the requirements of the RFID tag application, such as the physical size of the articles to be identified, their location, and the ability to reach them easily, tags may need to be read from a short distance or a long distance by an RFID reader. Such distances may vary from a few centimeters to ten or more meters. Additionally, in the U.S. and in other countries, the frequency range within which such tags are permitted to operate is limited. As an example, lower frequency bands, such as 125 KHz and 13.56 MHz, may be used for RFID tags in some applications. At this frequency range, the electromagnetic energy is less affected by liquids and other dielectric materials, but suffers from the limitation of a short interrogating distance. At higher frequency bands where RFID use is permitted, such as 915 MHz and 2.4 GHz, the RFID tags can be interrogated at longer distances, but they de-tune more rapidly as the material to which the tag is attached varies. It has also been found that at these higher frequencies, closely spaced RFID tags will de-tune each other as the spacing between tags is decreased.

There are a number of common situations where the RFID tags may be located inside enclosures. Some of these enclosures may have entirely or partially metal or metallized surfaces. Examples of enclosures include metal enclosures (e.g., shipping containers), partial metal enclosures (e.g., vehicles such as airplanes, buses, trains, and ships that have a housing made from a combination of metal and other materials), and non-metal enclosures (e.g., warehouses and buildings made of wood). Examples of objects with RFID tags that may be located in these enclosures include loose articles, packaged articles, parcels inside warehouses, inventory articles inside buildings, various goods inside retail stores, and various portable articles (e.g., passenger identification cards and tickets, baggage, cargo, individual life-saving equipment such as life jackets and masks) inside vehicles, etc.

The read range (i.e., the range of the interrogation and/or response signals) of RFID tags is limited. For example, some types of passive RFID tags have a maximum range of about twelve meters, which may be attained only in ideal free space conditions with favorable antenna orientation. In a real situation, the observed tag range is often six meters or less. Therefore, some of the enclosures described above may have dimensions that far exceed the read range of an individual RFID tag. Unless the RFID reader can be placed in close proximity to a target RFID tag in such an enclosure, the tag will not be activated and read. Additionally, metal surfaces of the enclosures present a serious obstacle for the RF signals that need to be exchanged between RFID readers and RFID tags, making RFID tags located behind those metal surfaces difficult or impossible to detect.

In addition to the above, the detection range of the RFID systems is typically limited by signal strength to short ranges, frequently less than about thirty centimeters for 13.56 MHz systems. Therefore, portable reader units may need to be moved past a group of tagged items in order to detect all the tagged items, particularly where the tagged items are stored in a space significantly greater than the detection range of a stationary or fixed single reader antenna. Alternately, a large reader antenna with sufficient power and range to detect a larger number of tagged items may be used. However, such an antenna may be unwieldy and may increase the range of the radiated power beyond allowable limits. Furthermore, these reader antennae are often located in stores or other locations where space is at a premium and it is expensive and inconvenient to use such large reader antennae. In another possible solution, multiple small antennae may be used but such a configuration may be awkward to set up when space is at a premium and when wiring is preferred or required to be hidden.

In the case of medical supplies and devices, it is desirable to develop accurate tracking, inventory control systems, and dispensing systems so that RFID tagged devices and articles may be located quickly should the need arise, and may be identified for other purposes, such as expiration dates. In the case of medical supply or dispensing cabinets used in a health care facility, a large number of medical devices and articles are located closely together, such as in a plurality of drawers. Cabinets such as these are typically made of metal, which can make the use of an external RFID system for identification of the stored articles difficult. In some cases, such cabinets are locked due to the presence of narcotics or other medical articles or apparatus within them that are subject to a high theft rate. Thus, manual identification of the cabinet contents is difficult due to the need to control access.

Providing an internal RFID system in such a cabinet can pose challenges. Where internal articles can have random placement within the cabinet, the RFID system must be such that there are no "dead zones" that the RFID system is unable to reach. In general, dead zones are areas in which the level of coupling between an RFID reader antenna and an RFID tag is not adequate for the system to perform a successful read of the tag. The existence of such dead zones may be caused by orientations in which the tag and the reader antennae are in orthogonal planes. Thus, articles placed in dead zones may not be detected thereby resulting in inaccurate tracking of tagged articles.

Often in the medical field, there is a need to read a large number of tags attached to articles in such an enclosure, and as mentioned above, such enclosures have limited access due to security reasons. The physical dimension of the enclosure may need to vary to accommodate a large number of articles or articles of different sizes and shapes. In order to obtain an accurate identification and count of such closely-located medical articles or devices, a robust electromagnetic energy field must be provided at the appropriate frequency within the enclosure to surround all such stored articles and devices to be sure that their tags are all are activated and read. Such medical devices may have the RFID tags attached to the outside of their containers and may be stored in various orientations with the RFID tag (and associated antenna) pointed upwards, sideways, downward, or at some other angle in a random pattern.

Generating such a robust EM energy field is not an easy task. Where the enclosure has a size that is resonant at the frequency of operation, it can be easier to generate a robust EM field since a resonant standing wave may be generated within the enclosure. However, in the RFID field the usable frequencies of operation are strictly controlled and are limited. It has been found that enclosures are desired for the storage of certain articles that do not have a resonant frequency that matches one of the allowed RFID frequencies. Thus, a robust EM field must be established in another way.

Additionally, where EM energy is introduced to such an enclosure for reading the RFID tags within, efficient energy transfer is of importance. Under static conditions, the input or injection of EM energy into an enclosure can be maximized with a simple impedance matching circuit positioned between the conductor delivering the energy and the enclosure. As is well known to those of skill in the art, such impedance matching circuits or devices maximize the power transfer to the enclosure while minimizing the reflections of power from the enclosure. Where the enclosure impedance changes due to the introduction or removal of articles to or from the enclosure, a static impedance matching circuit may not provide optimum energy transfer into the enclosure. If the energy transfer and resulting RF field intensity within the enclosure were to fall below a threshold level, some or many of the tags on articles within the enclosure would not be activated to identify themselves, leaving an ineffective inventory system.

It is a goal of many health care facilities to keep the use of EM energy to a minimum, or at least contained. The use of high-power readers to locate and extract data from RFID tags is generally undesirable in health care facilities, although it may be acceptable in warehouses that are sparsely populated with workers, or in aircraft cargo holds. Radiating a broad beam of EM energy at a large area, where that EM energy may stray into adjacent, more sensitive areas, is undesirable. Efficiency in operating a reader to obtain the needed identification information from tags is an objective. In many cases where RFID tags are read, hand-held readers are used. Such readers transmit a relatively wide beam of energy to reach all RFID tags in a particular location. While the end result of activating each tag and reading it may be accomplished, the transmission of the energy is not controlled except by the aim of the user. Additionally, this is a manual system that will require the services of one or more individuals, which can also be undesirable in facilities where staff is limited.

In a healthcare environment, there are many storage systems for medical articles that are used for different purposes and different patients. Some are open access storage systems. In most of these cases, and especially for emergency storage systems, they must be restocked upon use on a regular basis so that necessary medical articles will be available when needed. An example of such a medical article storage system is the medical cart used in rooms or in the hallways of healthcare facilities that are supplied to contain the medical articles prescribed or otherwise needed by the patients residing in the area of the cart. FIG. 23 shows an example of a patient medication cart 300. Such carts usually, but not always, include wheels 302 so that they are mobile, and often have multiple drawers 304 in which various medical articles are stored for one or more patients being treated in the vicinity of the cart. Only two drawers are indicated by numeral 304 in FIG. 1 so that the clarity of the drawing is not obscured. It is meant that the numeral 304 apply to all drawers. In this embodiment, each drawer has an external handle 306 provided for assisting a user in pulling the respective drawer 304 out of the cart frame 308.

Currently, hospital pharmacies dispense patient drugs and other medical articles into such a mobile cart to be delivered to the general floor where the patients are located. As mentioned, the cart has multiple drawer units that may be used for containing the medications of a plurality of patients. Each patient may have one or more drawers storing his or her medications and other medical articles. The current system allows open access by which a healthcare provider can take medications from a mobile or stationary cart for use with a patient other than the patient for whom those medications have been prepared and accumulated in the drawer of a cart. Multiple nurses have access to all the patient drawers and often "shop" for medications from one patient's drawer and give them to another patient. Errors can occur and often delays occur if a patient's medications are not in the drawer when the patient's nurse intends to administer them.

An example of a drawer 320 in the cabinet of FIG. 23 is shown in FIG. 24. The drawer has multiple pockets 322, in this case five. The pockets may have different sizes and shapes, and are used to store a patient's medications or other medical articles. For example, drawer 320 of FIG. 24 shows a vial of medication in one pocket, a blister pack of pills in another pocket, and in the longer pocket, a pre-loaded syringe is stored. Many other medical articles may be stored in the drawer for the patient, depending on the ailments causing the patient to be in the healthcare facility. Should the pre-loaded syringe be taken from the pocket for use on a different patient instead of being left available for the patient for whom it was prepared, the latter patient may suffer until the pharmacy can prepare a new own.

Hence, those skilled in the art have recognized a need for a better means of control over the dispensing of the medications and other medical articles to patients from mobile or stationary carts thus preventing errors as well as controlling improper drug retrieval. Another recognized need is to restrict the spread of electromagnetic energy in healthcare facilities. A further need has been recognized for managing the inventory of such carts so that they may be resupplied on a more timely basis. Yet another need has been recognized for monitoring the contents of such carts for expired and or recalled medical articles. Another need has been recognized for providing an accurate inventory detection system using a wireless system with smaller enclosures. The invention fulfills these needs and others.

SUMMARY OF THE INVENTION

Briefly and generally there is provided a system and a method to manage medical articles stored in a mobile dispensing cart and to control incorrect dispensing of those medical articles. There is provided a management system for managing inventory in a medical cart, the inventory comprising medical articles for dispensing to a patient, each of the medical articles being identified by a wireless data carrier which is responsive to electromagnetic energy (EM) of a frequency f1 in response to which the wireless data carrier provides identification data, the management system comprising a metallic enclosure having an internal reading area, the metallic enclosure located within the medical cart and having electrically conductive walls that completely surround the internal reading area, the enclosure having a natural frequency of resonance f2 which is different from the frequency f1 to which the data carriers are responsive, the data carriers not being operationally responsive to frequency f2, a probe disposed at an electrically-conductive wall of the metallic enclosure and configured to inject EM of a frequency f1 into the metallic enclosure, wherein the position of the probe in relation to electrically-conductive walls of the metallic enclosure is selected so that reflected EM of frequency f1 within the metallic enclosure is in phase at the probe position to thereby optimize power transfer at frequency f1 into the enclosure, an active impedance matching circuit coupled to the probe and configured to actively match more closely impedance of the probe to impedance of the metallic enclosure at frequency f1, a storage area located within the internal reading area of the metallic enclosure in the cart, the storage area configured to contain medical articles with associated data carriers identifying the medical articles, each data carrier being responsive to EM at frequency f1 but not operationally responsive to frequency f2, the storage area having an access control device that prevents access to the storage area when locked and allows access when unlocked, a receiving antenna disposed within the metallic enclosure and configured to receive the identification data provided by the data carriers in response to the injected EM, a processor, and a non-volatile memory in which is stored a data base that links a patient to medical articles stored for the patient in the storage area, and a data base that links a health care provider to the patient, wherein the processor is programmed to unlock the storage area for access by a health care provider linked to the patient, wherein the processor is programmed to detect and identify any medical article taken from the storage area, compare it to the patient data base, and if the medical article does not match the patient data base, provide an alarm.

In more detailed aspects, the memory comprises a data base of wireless data carrier identifications linked to medical article data in which one of those medical article data is an expiration date of the respective medical article, wherein the processor is further programmed to receive the data carrier identification data, access the data base of medical article data corresponding to that data carrier identifications and compare the expiration date of the identified medical articles to a selected date, and the processor being further programmed to provide a notice if the expiration date of a medical article falls on or before the selected date.

In yet other aspects, the memory includes a data base in which data pertaining to recalled articles are stored, and the processor further being programmed to compare the identification data of the medical articles in the storage container to the recalled article data base in the memory, and if the comparison shows that a medical article is recalled, to provide a notice of such recall status.

In method aspects according to the invention, there is provided a method of managing inventory in a medical cart, the inventory comprising medical articles for dispensing to a patient, each of the medical articles being identified by a wireless data carrier which is responsive to electromagnetic energy (EM) of a frequency f1 in response to which the wireless data carrier provides identification data, the management method comprising preparing a patient data base that includes all medical articles stored in the storage area for the patient, injecting electromagnetic energy of a frequency f1 into a metallic enclosure located within the cart with a probe, the metallic enclosure having electrically conductive walls, wherein the position of the probe in relation to the electrically conductive walls is selected so that reflected EM of frequency f1 within the metallic enclosure is in phase at the probe position to thereby optimize power transfer at frequency f1 into the enclosure, the electrically conductive walls completely surrounding an internal reading area of the enclosure, the enclosure having a natural frequency of resonance f2 which is different from the frequency f1 and to which a data carrier that is responsive to frequency f1 is not operationally responsive to frequency f2, wherein the storage area is located within the metallic enclosure, actively matching the impedance of a probe that is used to inject EM energy into the metallic enclosure more closely to impedance of the enclosure at frequency f1, controlling access to the storage area within the enclosure with a locking device, the storage area being inaccessible when the locking device is locked and accessible when the locking device is unlocked, receiving a request from a health care provider to have access to the storage area, comparing the patient to a patient data base to identify a health care provider assigned to the patient, unlocking the storage area if the health care provider requesting access matches as being assigned to the patient, after the locking device is re-locked, detecting and identifying any taken article from the storage area, comparing the taken article to the patient data base and if the taken article does not match the patient data base, providing an alarm.

In more detailed method aspects, the method further comprises determining if a medical article in the storage area is expired through locating an article expiration date from a medical article data base, comparing that expiration date to a selected expiration date, and providing a notice of expiration if the two dates match or if the expiration date of the medical article preceded the selected date. The method yet further comprises comparing the data of a medical article in the storage area to a recalled article data base on the memory, and if the comparison shows that the medical article is recalled, providing an indication of such recall status about the medical article.

The features and advantages of the invention will be more readily understood from the following detailed description that should be read in conjunction with the accompanying drawings.

BRIEF DESCRIPTION OF THE DRAWINGS

FIG. 9 shows an enclosure with two probes each with a connector for injecting EM energy into the enclosure, one probe being a TM probe and the other being a TE probe;

FIG. 10 shows a probe, a connector, and an attenuator that is used to improve the impedance match between the probe and the enclosure;

FIG. 11 shows a probe, a connector, and a passive matching circuit that is used to improve the impedance match between the probe and enclosure;

FIG. 12 shows an active matching circuit connected between a probe located in an enclosure and a transceiver, the active matching circuit comprising a tunable capacitor, a dual-directional coupler, multiple power sensors, and a comparator used to provide a closed-loop, variable matching circuit to improve the impedance match between the probe and the enclosure;

FIG. 27 is a block diagram flow chart of the creation of a medical article data base and a patient data base for a mobile cart;

DETAILED DESCRIPTION OF THE PREFERRED EMBODIMENTS

Figure 1:
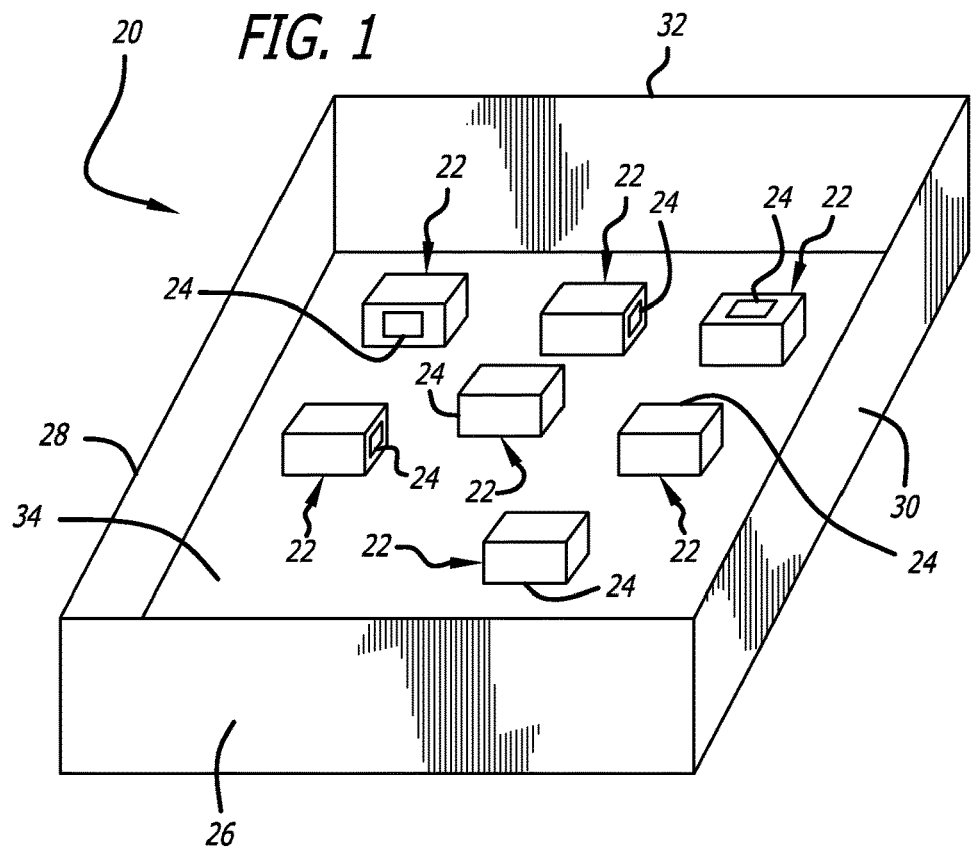
FIG. 1 is a schematic diagram of a drawer that may be positioned within a medical dispensing cabinet, showing the storage of a plurality of medical articles randomly positioned in the drawer, each of those articles having an integral RFID tag oriented randomly.

Referring now in more detail to the exemplary drawings for purposes of illustrating embodiments of the invention, wherein like reference numerals designate corresponding or like elements among the several views, there is shown in FIG. 1 a schematic representation of a partial enclosure 20 in which a plurality of medical articles 22 are stored, each with a respective RFID tag 24 that has a unique identification number. The partial enclosure may comprise a drawer having a front 26, a left side 28, a right side 30, a rear 32, and a bottom 34. These articles are randomly distributed in the drawer with the RFID tags facing in various and random directions.

As used in regard to the embodiments herein, "reader" and "interrogator" refer to a device that may read or write/ read. The data capture device is always referred to as a reader or an interrogator regardless of whether it can only read or is also capable of writing. A reader typically contains a radio frequency module (a transmitter and a receiver, sometimes referred to as a "transceiver"), a control unit, and a coupling element (such as an antenna or antennae) to the RFID tag. Additionally, many readers include an interface for forwarding data elsewhere, such as an RS-232 interface. The reader, when transmitting, has an interrogation zone within which an RFID tag will be activated. When within the interrogation zone, the RFID tag will draw its power from the electrical/magnetic field created in the interrogation zone by the reader. In a sequential RFID system (SEQ), the interrogation field is switched off at regular intervals. The RFID tag is programmed to recognize these "off" gaps and they are used by the tag to send data, such as the tag's unique identification number. In some systems, the tag's data record contains a unique serial number that is incorporated when the tag is manufactured and which cannot be changed. This number may be associated in a data base with a particular article when the tag is attached to that article. Thus, determining the location of the tag will then result in determining the location of the article to which it is attached. In other systems, the RFID tag may contain more information about the article to which it is attached, such as the name or identification of the article, its expiration date, its dose, the patient name, and other information. The RFID tag may also be writable so that it can be updated.

As used in regard to the embodiments herein, "tag" is meant to refer to an RFID transponder. Such tags typically have a coupling element, such as an antenna, and an electronic microchip. The microchip includes data storage, also referred to as memory.

Figure 2:
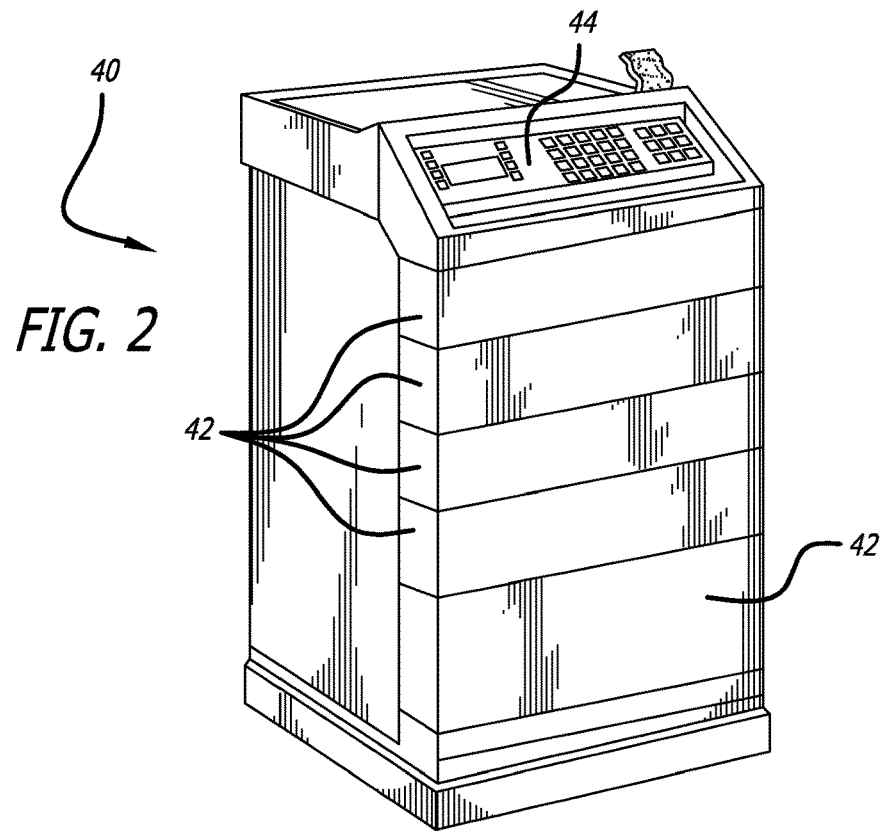
FIG. 2 is a perspective view of a medication dispensing cabinet having five drawers, one of which is similar to the schematic view of FIG. 1, the cabinet also having an integral computer for controlling access to the cabinet and performing inventory tracking by periodically reading any RFID tags placed on articles stored within the cabinet, and for reporting the identified articles to a remote computer.

FIG. 2 presents a representative medical dispensing cabinet 40 comprising a plurality of movable drawers 42. In this embodiment, there are five drawers that slide outwardly from the cabinet so that access is provided to the contents of the drawers. FIG. 1 is a schematic diagram of a representative drawer that may be positioned within the cabinet of FIG. 2 for sliding outward to provide access to the drawer's contents and for sliding inward into the cabinet to secure the drawer's contents. The cabinet also comprises an integral computer 44 that may be used to control access to the drawers and to generate data concerning access and contents, and to communicate with other systems. In this embodiment, the computer generates data concerning the number and type of articles in the drawers, the names of the patients for whom they have been prescribed, the prescribed medications and their prescribed administration dates and times, as well as other information. In a simpler system, the computer may simply receive unique identification numbers from stored articles and pass those identification numbers to an inventory control computer that has access to a data base for matching the identification numbers to article descriptions.

Such a cabinet may be located at a nursing station on a particular floor of a health care institution and may contain the prescriptions for the patients of that floor. As prescriptions are prepared for the patients of that floor, they are delivered and placed into the cabinet 40. They are logged into the integral computer 44, which may notify the pharmacy of their receipt. A drawer may also contain non-prescription medical supplies or articles for dispensing to the patients as determined by the nursing staff. At the appropriate time, a nurse would access the drawer in which the medical articles are stored through the use of the computer 44, remove a particular patient's prescriptions and any needed non-prescription articles, and then close the drawer so that it is secured. In order to access the cabinet, the nurse may need to provide various information and may need a secure access code. The drawers 42 may be locked or unlocked, as conditions require.

The computer 44 in some cases may be in communication with other facilities of the institution. For example, the computer 44 may notify the pharmacy of the health care institution that a patient's prescription has been removed from the cabinet for administration at a particular day and time. The computer may also notify the finance department of the health care institution of the removal of prescriptions and other medical articles for administration to a particular patient. This medication may then be applied to the patient's account. Further, the computer 44 may communicate to administration for the purpose of updating a patient's Medication Administration Record (MAR), or e-MAR. The medication cabinet 40 computer 44 may be wirelessly connected to other computers of the health care institution or may have a wired connection. The cabinet may be mounted on wheels and may be moved about as needed or may be stationary and unable to move.

Figure 3:
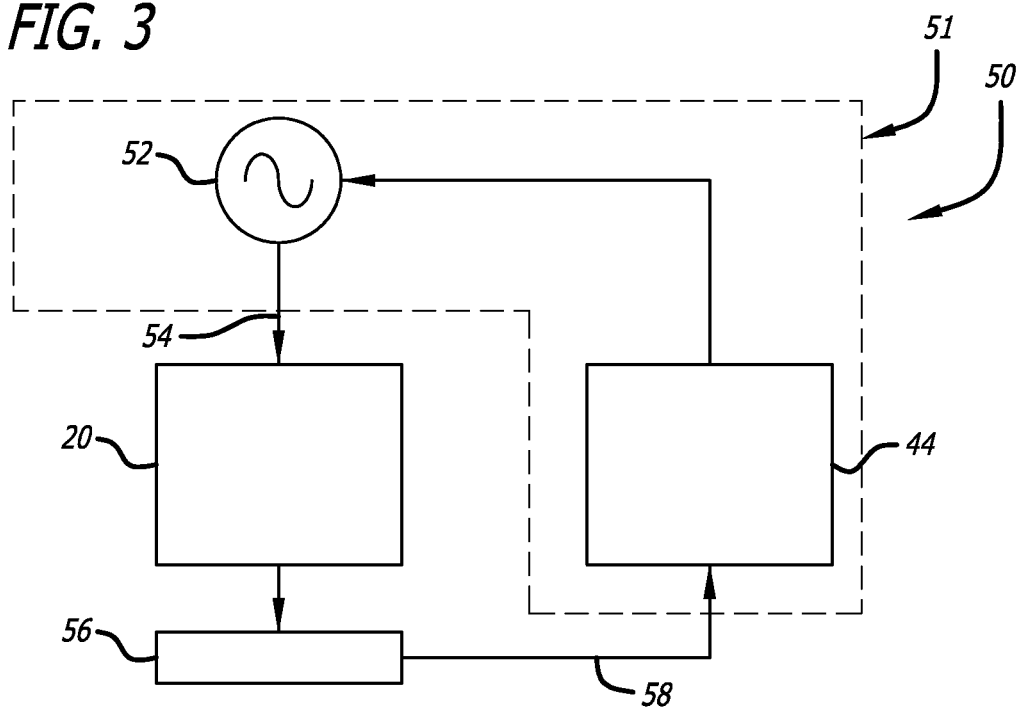
FIG. 3 is a block and flow diagram showing an embodiment in which an RFID reader transmits activating EM energy into a drawer containing RFID tags with a single transmitting antenna, receives the data output from the activated RFID tags with a single receiving antenna, a computer controlling the transmission of activating energy and receiving the data from the activated RFID tags for processing.
Figure 4:
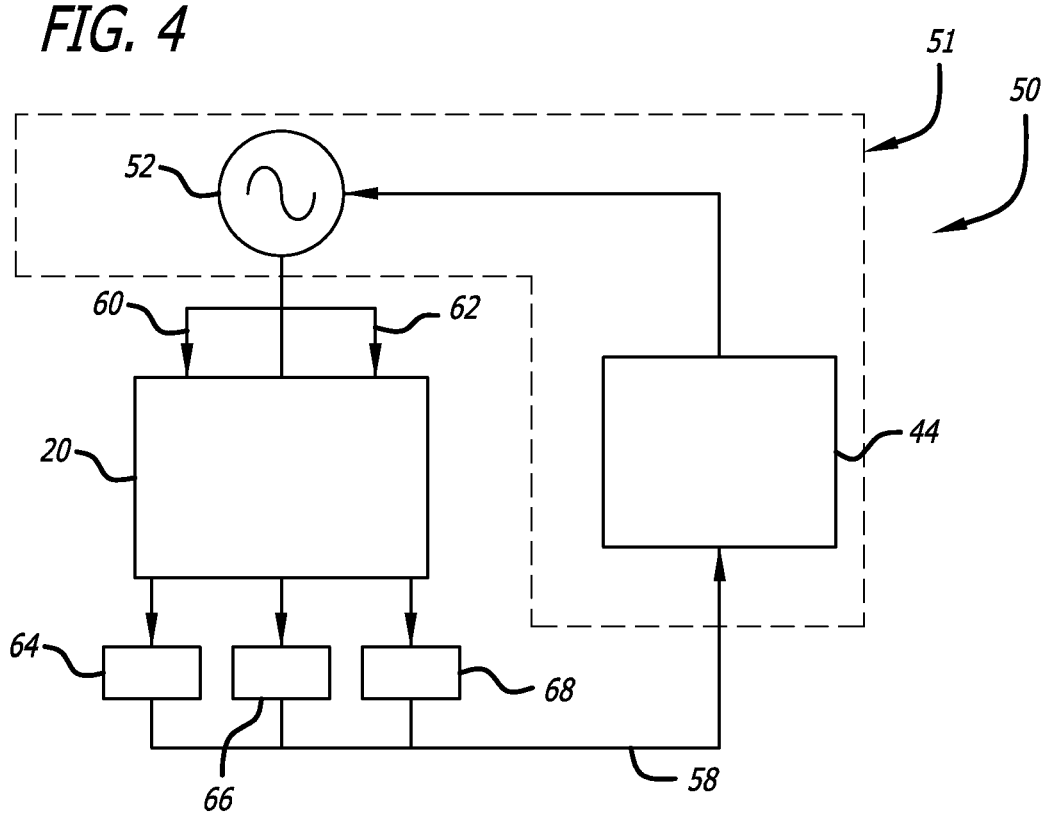
FIG. 4 is a block and flow diagram similar to FIG. 3 showing an embodiment in which an RFID reader transmits activating EM energy into a drawer containing RFID tags with two transmitting antennae, receives the data output from the activated RFID tags with three receiving antennae, and as in FIG. 3, a computer controlling the transmission of activating energy and receiving the data from the activated RFID tags for processing.

Systems that use RFID tags often employ an RFID reader in communication with one or more host computing systems that act as depositories to store, process, and share data collected by the RFID reader. Turning now to FIGS. 3 and 4, a system and method 50 for tracking articles are shown in which a drawer 20 of the cabinet 40 of FIG. 2 is monitored to obtain data from RFID tags disposed with articles in that drawer. As mentioned above, a robust field of EM energy needs to be established in the storage site so that the RFID tags mounted to the various stored articles will be activated, regardless of their orientation.

In FIGS. 3 and 4, the tracking system 50 is shown for identifying articles in an enclosure and comprises a transmitter 52 of EM energy as part of an RFID reader. The transmitter 52 has a particular frequency, such as 915 MHz, for transmitting EM energy into a drawer 20 by means of a transmitting antenna 54. The transmitter 52 is configured to transmit the necessary RFID EM energy and any necessary timing pulses and data into the enclosure 20 in which the RFID tags are disposed. In this case, the enclosure is a drawer 20. The computer 44 of an RFID reader 51 controls the EM transmitter 52 to cycle between a transmit period and a non-transmit, or off, period. During the transmit period, the transmitted EM energy at or above a threshold intensity level surrounds the RFID tags in the drawer thereby activating them. The transmitter 52 is then switched to the off period during which the RFID tags respond with their respective stored data.

The embodiment of FIG. 3 comprises a single transmitting probe antenna 54 and a single receiving antenna 56 oriented in such a manner so as to optimally read the data transmitted by the activated RFID tags located inside the drawer 20. The single receiving antenna 56 is communicatively coupled to the computer 44 of the reader 50 located on the outside of the drawer 20 or on the inner bottom of the drawer. Other mounting locations are possible. Coaxial cables 58 or other suitable signal links can be used to couple the receiving antenna 56 to the computer 44. A wireless link may be used in a different embodiment. Although not shown in the figures, those skilled in the art will recognize that various additional circuits and devices are used to separate the digital data from the RF energy, for use by the computer. Such circuits and devices have not been shown in FIGS. 3 and 4 to avoid unneeded complexity in the drawing.

The embodiment of FIG. 4 is similar to the embodiment of FIG. 3 but instead uses two transmitting probe antennae 60 and 62 and three receiving antennae 64, 66, and 68. The configuration and the number of transmitting probe antennae and receiving antennae to be used for a system may vary based at least in part on the size of the enclosure 20, the frequency of operation, the relationship between the operation frequency and the natural resonance frequency of the enclosure, and the expected number of RFID tags to be placed in it, so that all of the RFID tags inside the enclosure can be reliably activated and read. The location and number of RFID reader components can be dependent on the particular application. For example, fewer components may be required for enclosures having a relatively small size, while additional components, such as shown in FIG. 4, may be needed for larger enclosures. Although shown in block form in FIGS. 3 and 4, it should be recognized that each receiving antenna 56, 64, 66, and 68 of the system 50 may comprise a sub-array in a different embodiment.

The transmit antennae (54, 60, and 62) and the receive antennae (56, 64, 66, and 68) may take different forms. In one embodiment as is discussed in more detail below, a plurality of "patch" or microstrip antennae were used as the reader receiving antennae and were located at positions adjacent various portions of the bottom of the drawer while the transmit antennae were wire probes located at positions adjacent portions of the top of the drawer. It should be noted that in the embodiments of FIGS. 3 and 4, the RFID reader 50 may be permanently mounted in the same cabinet at a strategic position in relation to the drawer 20.

One solution for reliably interrogating densely packed or randomly oriented RFID tags in an enclosure is to treat the enclosure as a resonant cavity. Establishing a resonance within the cavity enclosure can result in a robust electromagnetic field capable of activating all RFID tags in the enclosure. This can be performed by building an enclosure out of electrically conductive walls and exciting the metallic enclosure, or cavity, using a probe or probes to excite transverse electric (TE) or transverse magnetic (TM) fields in the cavity at the natural frequency of resonance of the cavity. This technique will work if the cavity dimensions can be specifically chosen to set up the resonance at the frequency of operation or if the frequency of operation can be chosen for the specific enclosure size. Since there are limited frequency bands available for use in RFID applications, varying the RFID frequency is not an option for many applications. Conversely, requiring a specific set of physical dimensions for the enclosure so that the natural resonant frequency of the enclosure will equal the available RFID tag activating frequency will restrict the use of this technique for applications where the enclosure needs to be of a specific size. This latter approach is not practical in view of the many different sizes, shapes, and quantities of medical articles that must be stored.

Figure 5:
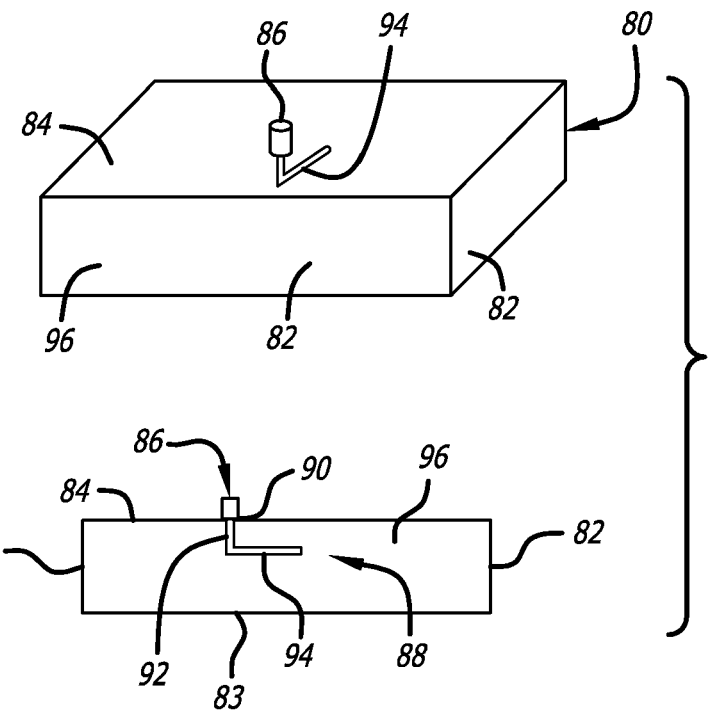
FIG. 5 shows an enclosure with a single probe and a connector, the probe being configured to inject EM energy into the enclosure and excite a TE mode.

Referring now to FIG. 5, a rectangular enclosure 80 is provided that may be formed as part of a medical cabinet, such as the cabinet shown in FIG. 2. It may be embodied as a frame disposed about a non-metallic drawer in such a cabinet. The enclosure 80 is formed of metallic or metallized walls 82, floor 83, and ceiling 84 surfaces, all of which are electrically conductive. All of the walls 82, floor 83, and ceiling 84 may also be referred to herein as "walls" of the enclosure. FIG. 5 also shows the use of an energy coupling or probe 86 located at the top surface 84 of the enclosure 80. In this embodiment, the probe takes the form of a capacitor probe 88 in that the probe 88 has a first portion 94 that proceeds axially through a hole 90 in the ceiling 84 of the enclosure. The purpose of the coupling is to efficiently transfer the energy from the source 52 (see FIGS. 3 and 4) to the interior 96 of the enclosure 80. The size and the position of the probe are selected for effective coupling and the probe is placed in a region of maximum field intensity. In FIG. 5, a TEN mode is established through the use of capacitive coupling. The length and distance of the bent portion 94 of the probe 88 affects the potential difference between the probe and the enclosure 80.

Figure 6:
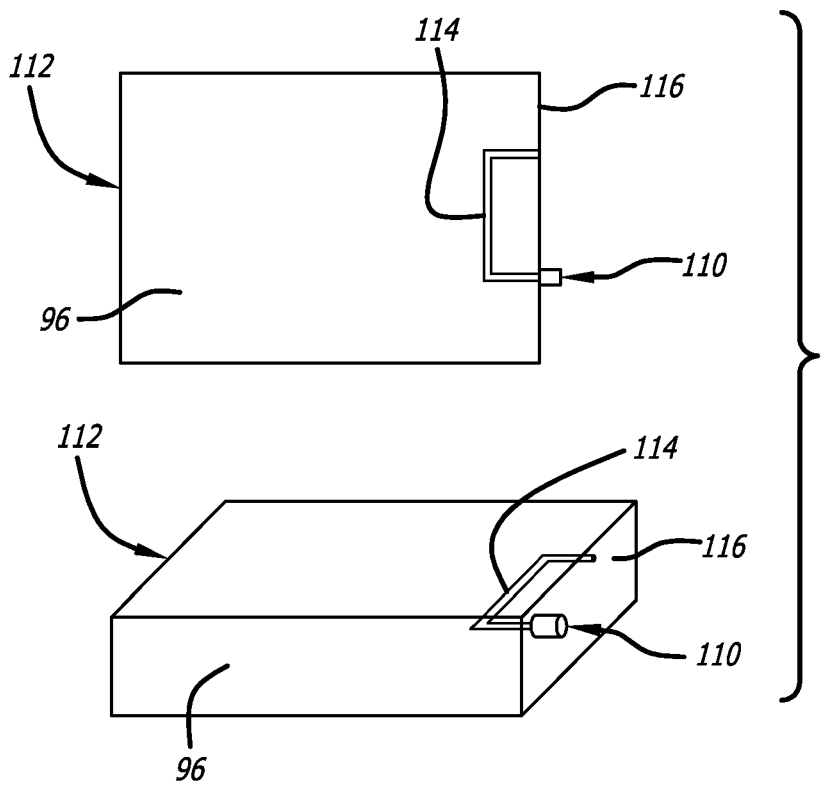
FIG. 6 shows an enclosure with a single probe and a connector, the probe being configured to inject EM energy into the enclosure and excite a TM mode.

Similarly, FIG. 6 presents an inductive coupling 110 of the external energy to an enclosure 112. The coupling takes the form of a loop probe 114 mounted through a side wall 116 of the enclosure. The purpose of this probe is to establish a TMoi mode in the enclosure.

Figure 7:
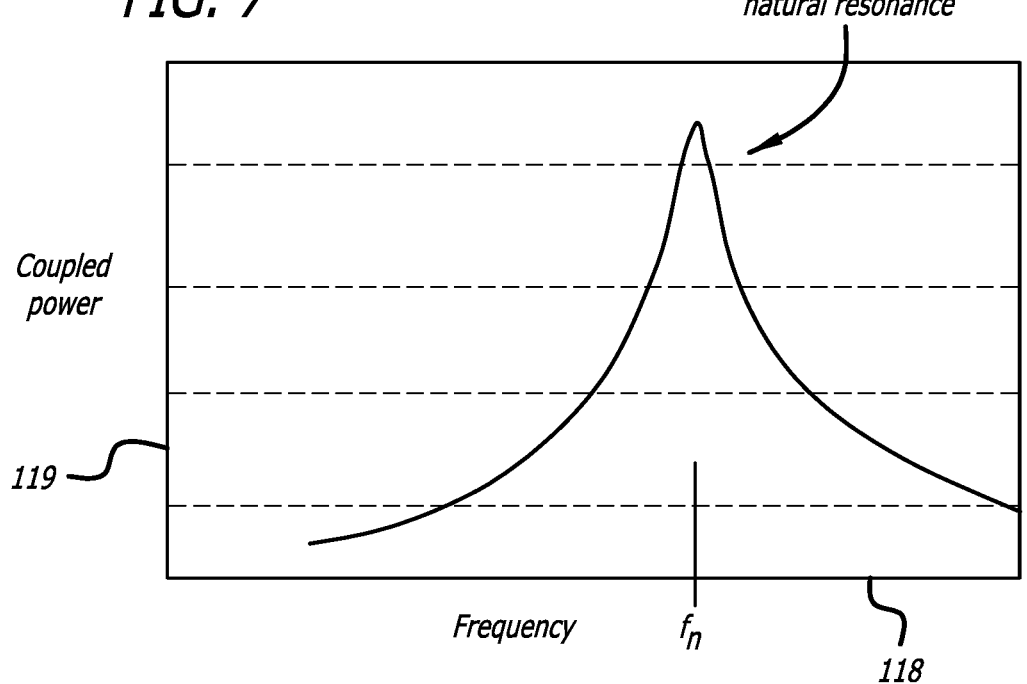
FIG. 7 shows a plot of coupled power in an enclosure as a function of frequency for a resonant enclosure where $F_n$ is the natural resonance frequency of the enclosure.

The rectangular enclosures 80 and 112 shown in FIGS. 5 and 6 each have a natural frequency of resonance $f_n$, shown in FIG. 7 and indicated on the abscissa axis 118 of the graph by $f_n$. This is the frequency at which the coupled power in the enclosure is the highest, as shown on the ordinate axis 119 of the graph. If the injected energy to the enclosure does not match the $f_n$ frequency, the coupled power will not benefit from the resonance phenomenon of the enclosure. In cases where the frequency of operation cannot be changed, and is other than $f_n$, and the size of the enclosure cannot be changed to obtain an $f_n$ that is equal to the operating frequency, another power coupling apparatus and method must be used. In accordance with aspects of the invention, an apparatus and method are provided to result in a forced resonance $f_f$ within the enclosure to obtain a standing wave within the enclosure with constructive interference. Such a standing wave will establish a robust energy field within the enclosure strong enough to activate all RFID tags residing therein.

Figure 8:
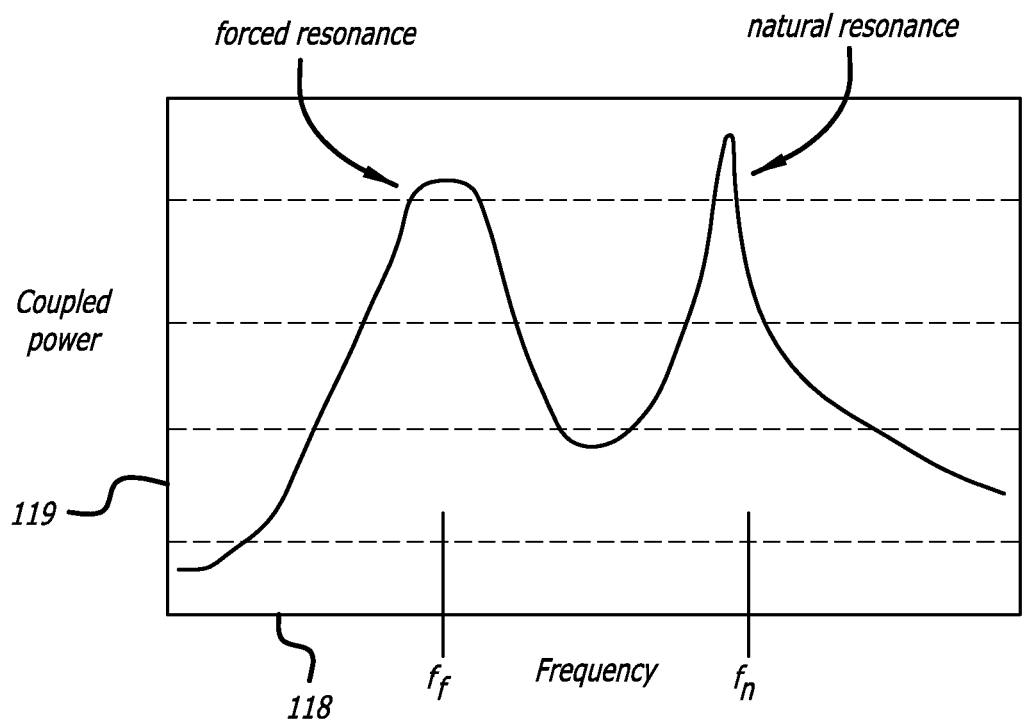
FIG. 8 shows a plot of coupled power (ordinate axis) in an enclosure as a function of frequency (abscissa axis), where $f_f$ is a forced resonance frequency, or otherwise referred to as a frequency that is not equal to the resonant frequency of the enclosure, and $f_n$ is the natural resonant frequency of the enclosure, showing the establishment of a robust field of coupled power in the enclosure at the $f_f$ frequency.

When an EM wave that is resonant with the enclosure enters, it bounces back and forth within the enclosure with low loss. As more wave energy enters the enclosure, it combines with and reinforces the standing wave, increasing its intensity (constructive interference). Resonation occurs at a specific frequency because the dimensions of the cavity are an integral multiple of the wavelength at the resonance frequency. In the present case where the injected energy is not at the natural resonance frequency $f_n$ of the enclosure, a solution in accordance with aspects of the invention is to set up a "forced resonance" in an enclosure. This forced resonance is different from the natural resonance of the enclosure in that the physical dimensions of the enclosure are not equal to an integral multiple of the wavelength of the excitation energy, as is the case with a resonant cavity. A forced resonance can be achieved by determining a probe position, along with the probe length to allow for energy to be injected into the cavity such that constructive interference results and a standing wave is established. The energy injected into the enclosure in this case will set up an oscillatory field region within the cavity, but will be different from a standing wave that would be present at the natural resonance frequency $f_n$ of a resonant cavity. The EM field excited from this forced resonance will be different than the field structure found at the natural resonance of a resonant cavity, but with proper probe placement of a probe, a robust EM field can nevertheless be established in an enclosure for RFID tag interrogation. Such is shown in FIG. 8 where it will be noted that the curve for the forced resonance $f_f$ coupled power is close to that of the natural resonance $f_n$.

Turning now to FIG. 9, an enclosure 120 having two energy injection probes is provided. The first probe 86 is capacitively coupled to the enclosure 120 in accordance with FIG. 5 to establish a $TE_{01}$ mode. The second probe 114 is inductively coupled to the enclosure 120 in accordance with FIG. 6 to establish a $TM_{01}$ mode. These two probes are both coupled to the enclosure to inject energy at a frequency $f_f$ that is other than the natural resonance frequency $f_n$ of the enclosure. The placement of these probes in relation to the ceiling 126 and walls 128 of the enclosure will result in a forced resonance within the enclosure 120 that optimally couples the energy to the enclosure and establishes a robust EM field within the enclosure for reading RFID tags that may be located therein. The placement of these probes in relation to the walls of the enclosure, in accordance with aspects of the invention, result in the forced resonance curve $f_f$ shown in FIG. 8.

Referring briefly to FIG. 10, an impedance matching circuit 121 is shown that functions to match the impedance of a source of energy 122 to the enclosure 120. The impedance matching circuit is located between the coaxial cable 122 that feeds activating energy to the enclosure 120 and the capacitively coupled probe 88 through a hole in the metallic ceiling 126 of the enclosure. While the hole is not shown in the drawing of FIG. 10, the insulator 123 that electrically insulates the probe from the metallic ceiling is shown. In this case, the matching circuit 121 consists of only a resistive attenuator 124 used to reduce reflections of energy by the enclosure 120. However, as will be appreciated by those of skill in the art, capacitive and inductive components are likely to exist in the enclosure and in the coupling 88. FIG. 11 on the other hand presents an impedance matching circuit 124 having passive reactive components for use in matching the impedance of the coaxial cable/energy source 122 and the enclosure 120. In this exemplary impedance matching circuit 124, an inductive component 125 and a capacitive component 127 are connected in series, although other configurations, including the addition of a resistive component and other connection configurations are possible.

Passive components such as resistors, inductors, and capacitors shown in FIGS. 10 and 11 can be used to form matching circuits to match the impedances of the energy source and the enclosure. This will aid in coupling power into the enclosure. However, the passive matching circuit will improve the impedance match for a specific enclosure loading, such as an empty enclosure, partially loaded, or fully loaded enclosure. But as the enclosure contents are varied, the impedance match may not be optimized due to the variation in contents in the enclosure causing the impedance properties of the enclosure to change.

This non-optimal impedance match caused by variation in enclosure loading can be overcome by the use of an active impedance matching circuit which utilizes a closed loop sensing circuit to monitor forward and reflected power. Referring now to FIG. 12, an active matching circuit 130 is provided that comprises one or several fixed value passive components such as inductors 132, capacitors 134, or resistors (not shown). In addition, one or several variable reactance devices, such as a tunable capacitor 134, are incorporated into the circuit; these tunable devices making this an active impedance matching circuit. The tunable capacitor 134 can take the form of a varactor diode, switched capacitor assembly, MEMS capacitor, or BST (Barium Strontium Titanate) capacitor. A control voltage is applied to the tunable capacitor 134 and varied to vary the capacitance provide by the device. The tunable capacitor 134 provides the capability to actively change the impedance match between the probe 140 and the enclosure 142.

To complete the active matching circuit, a dual directional coupler 144 along with two power sensors 146 can be incorporated. The dual directional coupler 144 and the power sensors 146 provide the ability to sense forward and reflected power between the RFID transceiver 148 and the active matching circuit 130 and enclosure 142. Continuous monitoring of the ratio of forward and reflected power by a comparator 150 provides a metric to use to adjust the tunable capacitor 134 to keep the probe 140 impedance matched to the enclosure 142. An ability to continuously monitor and improve the impedance match as the contents of the enclosure are varied is provided with the active matching circuit 130.

Figure 13:
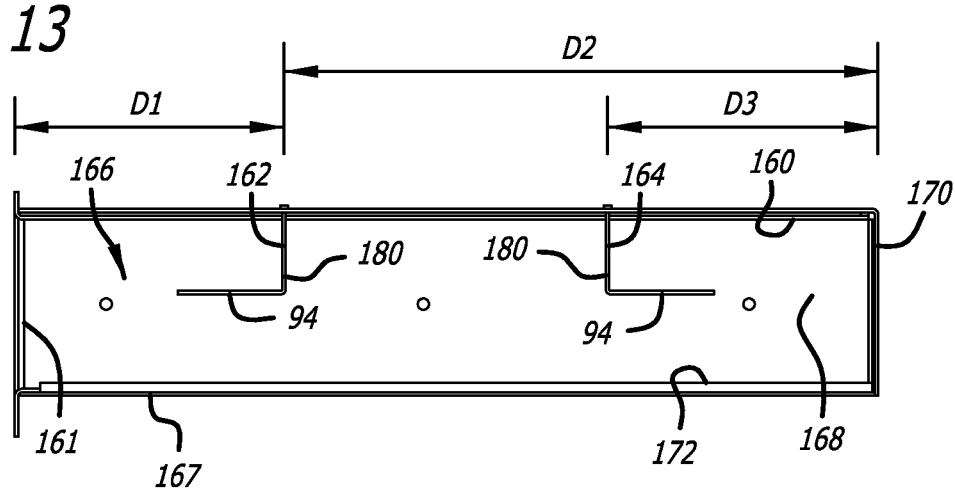
FIG. 13 provides a side cross-sectional view of the cabinet of FIG. 2 at the location of a drawer with the drawer removed for clarity, showing the placement of two probe antennae in a "ceiling mount" configuration for establishing a robust EM field in the drawer when it is in place in the cabinet in the closed position.

Referring now to the side cross-sectional view of FIG. 13, two ceiling-mounted 160 probe antennae 162 and 164 are shown mounted within an enclosure, which may also be referred to herein as a cavity 166, which in this embodiment, operates as a Faraday cage. As shown, the Faraday cage 166 comprises walls (one of which is shown) 168, a back 170, a floor 172, a ceiling 160, and a front 161 (only the position of the front wall is shown). All surfaces forming the cavity are electrically conductive, are electrically connected with one another, and are structurally formed to be able to conduct the frequency of energy $f_r$ injected by the two probes 162 and 164. In this embodiment, the cavity 166 is constructed as a metal frame 167 that may form a part of a medical supply cabinet similar to that shown in FIG. 2. Into that metal frame may be mounted a slidable drawer. The slidable drawer in this embodiment is formed of electrically inert material, that is, it is not electrically conductive, except for the front. When the drawer is slid into the cabinet to a closed configuration, the electrically conductive front panel of the drawer comes into electrical contact with another part or parts of the metallic frame 167 thereby forming the front wall 161 of the Faraday cage 167.

The amount of penetration or retention into the cavity by the central conductor 180 of each probe is selected so as to achieve optimum coupling. The length of the bent portion 94 of the probe is selected to result in better impedance matching. The position of the probe in relation to the walls of the cavity is selected to create a standing wave in the cavity. In this embodiment, the probe antennae 162 and 164 have been located at a particular distance D1 and D3 from respective front 161 and back 170 walls. These probe antennae, in accordance with one aspect of the invention, are only activated sequentially after the other probe has become inactivated. It has been found that this configuration results in a standing wave where the injected energy waves are in phase so that constructive interference results.

Figure 14:
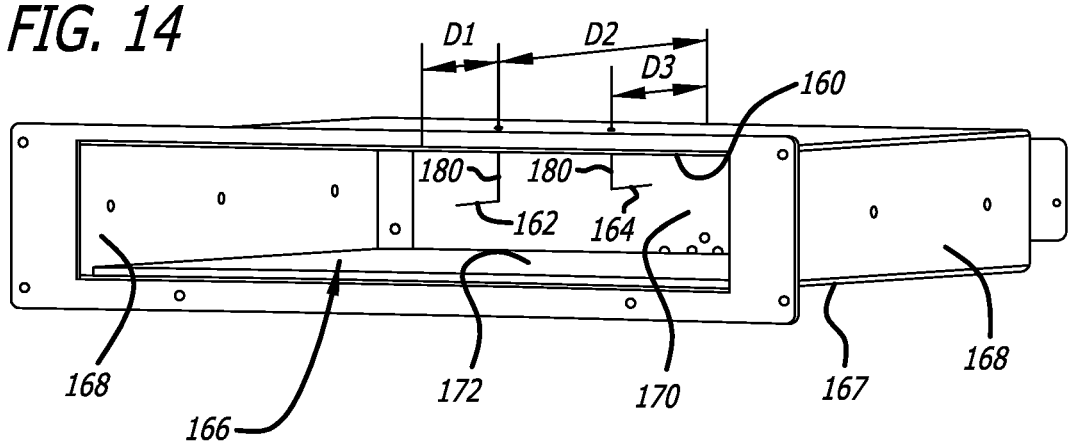
FIG. 14 is a perspective view of the metallic enclosure showing the probe configuration of FIG. 13 again showing the two probe antennae for establishing a robust EM field in a drawer to be inserted.

FIG. 14 is a front perspective view of the probe configuration of FIG. 13 again showing the two probe antennae 162 and 164 located in a Faraday-type enclosure 166 for establishing a robust EM field in an article storage drawer to be inserted. It should be noted again that the Faraday cavity 166 is constructed as a metallic frame 167. In this figure, the cavity is incomplete in that the front surface of the "cage" is missing. In one embodiment, this front surface is provided by an electrically conductive front panel of a slidable drawer. When the drawer is slid into the cabinet, the front panel will make electrical contact with the other portions of the metallic frame 167 thereby completing the Faraday cage 166, although other portions of the drawer are plastic or are otherwise non-electrically conductive. In the embodiment discussed and shown herein, the two probe antennae 162 and 164 are both located along a centerline between the side walls 166 and 168 of the frame 166. The enclosure in one embodiment was 19.2 inches wide with the probe antennae spaced 9.6 inches from each side wall. This centered location between the two side walls was for convenience in the case of one embodiment. The probes may be placed elsewhere in another embodiment. In this embodiment, the spacing of the probes 162 and 164 from each other is of little significance since they are sequentially activated. Although not shown, two receiving antennae will also be placed into the Faraday cage 166 to receive response signals from the activated RFID tags residing within the cavity 166.

It will also be noted from reference to the figures that the probes each have a bent portion used for capacitive coupling with the ceiling 160 of the cavity, as is shown in FIG. 13. The front probe 162 is bent forward while the back probe 164 is bent rearward A purpose for this configuration was to obtain more spatial diversity and obtain better coverage by the EM field established in the drawer. Other arrangements may be possible to achieve a robust field within the cavity 166. Additionally two probes were used in the particular enclosure 166 so that better EM field coverage of the enclosure 166 would result.

Figure 15:
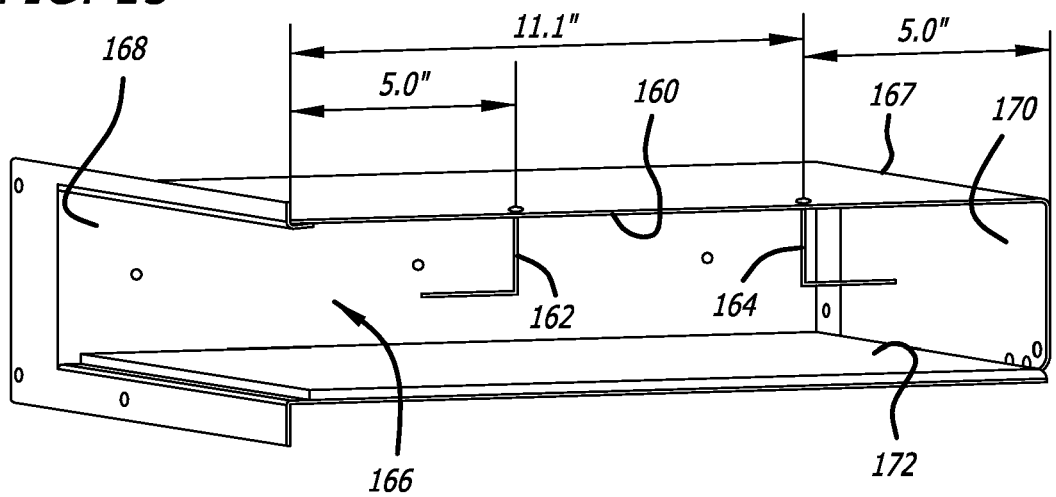
FIG. 15 is a cutaway perspective side view of the metallic enclosure or frame in which are mounted the dual probe antennae of FIGS. 13 and 14 with the drawer removed for clarity.

FIG. 15 is a cutaway perspective side view of the dual probe antennae 162 and 164 of FIGS. 13 and 14, also with the drawer removed for clarity. The front probe 162 is spaced from the left side wall by ½λ of the operating frequency $F_f$ as shown. It will be noted that the probes each have a bent portion used for capacitive coupling with the ceiling 160 of the enclosure 166 as shown in FIG. 13. The front probe 162 is bent forward for coupling with the more forward portion of the enclosure while the back probe 164 is bent rearward for coupling with the more rearward portion of the enclosure 166 to obtain more spatial diversity and obtain better coverage by the EM field in the drawer. Other arrangements may be possible to achieve a robust field and further spatial diversity and coverage within the enclosure.

Figure 16:
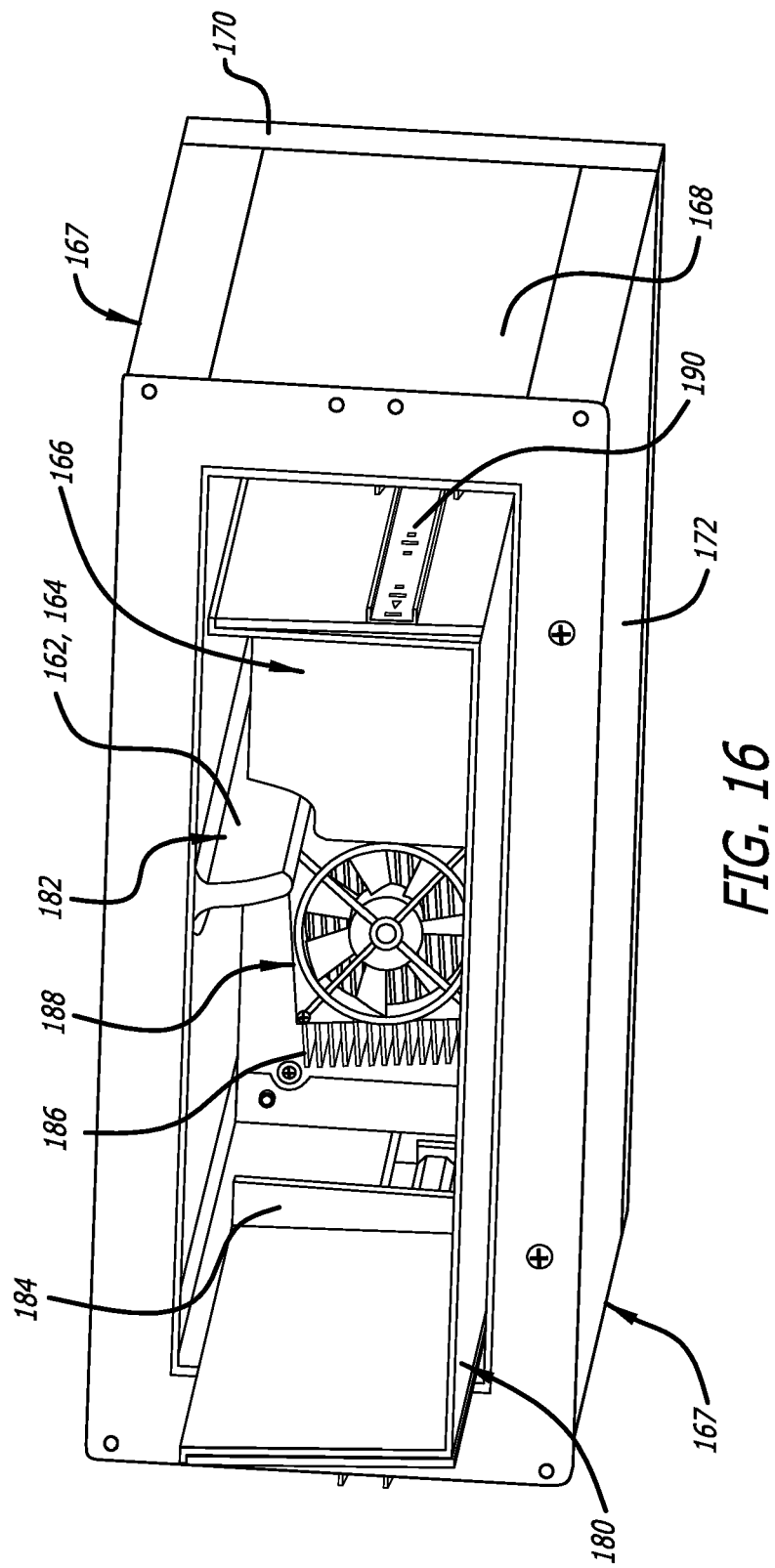
FIG. 16 is a frontal perspective view of the view of FIG. 14 with a cutaway plastic drawer in place in the metallic enclosure and further showing the dual ceiling mount probe antennae protected by an electromagnetically inert protective cover, and further showing cooling system components mounted at the back of the cabinet near the drawer's back, the drawing also showing a partial view of a drawer slide mechanism for ease in sliding the drawer between open and closed positions in the cabinet, the drawer front and rear panels having been cutaway in this view.

FIG. 16 is a frontal upward-looking perspective view of the frame 167 forming a Faraday cage 166 showing a portion of a drawer 180 that has been slidably mounted within the frame 167. The front metallic panel of the drawer has been removed so that its sliding operation can be more clearly seen. It will also be noted that the dual ceiling mount probe antennae 162 and 164 have been covered and protected by an electromagnetically inert protective cover 182. The drawer is formed of a non-metallic material, such as a plastic or other electromagnetic inert material having a low RF constant. The back 184 of the drawer has also been cut away so that a cooling system comprising coils 186 and a fan 188 located in the back of the frame 167 can be seen. In this case, the drawer 180 is slidably mounted to the Faraday cage frame with metallic sliding hardware 190. The sliding hardware of the drawer is so near the side of the frame 167 of the enclosure 166 and may be in electrical contact with the metallic slide hardware of the side walls 168 of the enclosure that these metallic rails will have only a small effect on the EM field established within the enclosure.

Figure 17:
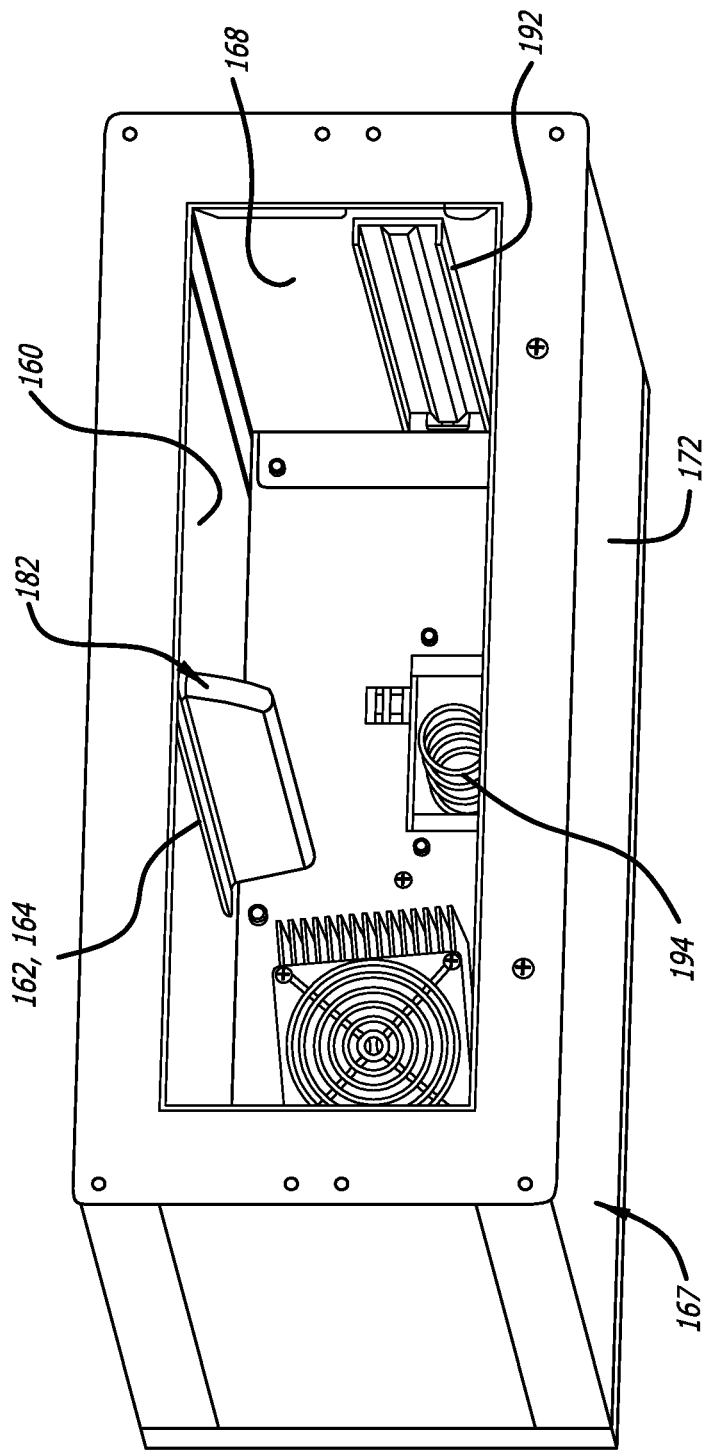
FIG. 17 is a frontal perspective view at the opposite angle from that of FIG. 16 with the plastic drawer completely removed showing the dual ceiling mount probe antennae protected by the EM inert protective cover mounted to the metallic enclosure, and further showing the cooling system components of FIG. 16 mounted at the back of the cabinet as a spring loading feature to automatically push the drawer to the open position when the drawer's latch is released, the figure also showing a mounting rail for receiving the slide of the drawer.

FIG. 17 is an upward looking, frontal perspective view at the opposite angle from that of FIG. 16; however, the drawer has been removed. The frame 167 in this embodiment includes a mounting rail 192 for receiving the slide of the drawer 180. In this embodiment, the mounting rail is formed of a metallic material; however, it is firmly attached to a side 168 of the Faraday cage and thus is in electrical continuity with the cage. The figure also shows a spring mechanism 194 used to assist in sliding the drawer outward so that access to the articles stored in the drawer may be gained. The spring is configured to push automatically the drawer outward when the drawer's latch is released.

Figure 18:
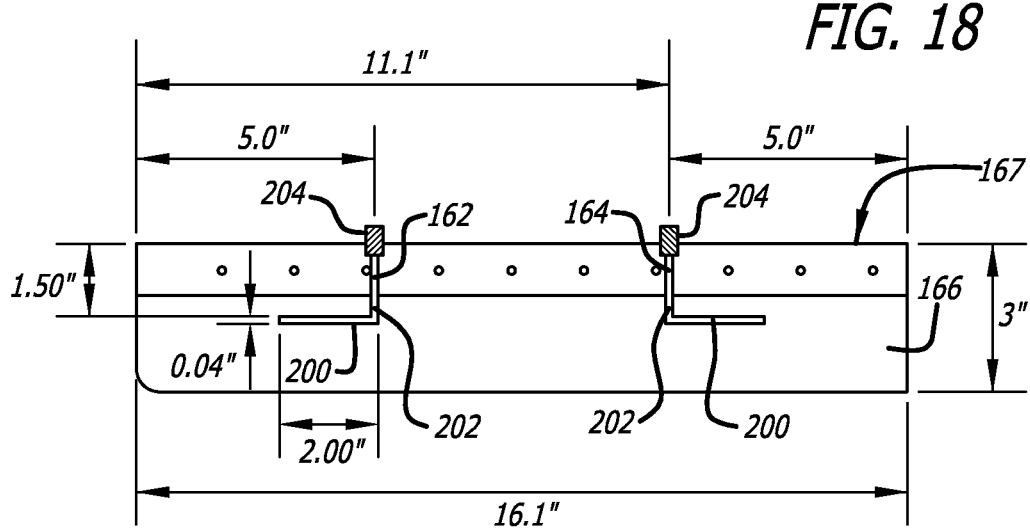
FIG. 18 is a schematic view with measurements in inches of the placement of two $TE_{01}$ mode probes in the top surface of the enclosure shown in FIGS. 13-15.

FIG. 18 is a schematic view showing measurements of the placement of two $TE_{01}$ mode capacitive coupling probes 162 and 164 in the ceiling 160 of the frame 167 shown in FIGS. 13-15. In this embodiment, the frequency of operation with the RFID tags is 915 MHz, which therefore has a wavelength of 0.32764 meters or 1.07494 feet. One-half wavelength is therefore 0.16382 meters or 6.4495 inches. The length of the capacitive coupling bent portion 200 of each of the probes is 5.08 cm or 2.00 in. The length of the axial extension 202 of the probes into the enclosure is 3.81 cm or 1.50 in., as measured from the insulator 204 into the enclosure 166. The probe configuration and placement in the embodiment was based on an operation frequency of 915 MHz. In one embodiment, the enclosure 166 had a depth of 16.1 inches (40.89 cm), a width of 19.2 inches (48.77 cm), and a height of 3 inches (7.62 cm). It was found that the optimum probe placements for this size and shape (rectangular) enclosure and for the 915 MHz operating frequency were: the front probe was spaced from the front wall by 5.0 inches (12.7 cm) and the rear probe was spaced from the back wall by 5.0 inches (12.7 cm). As discuss above, the probes in this embodiment would only be activated sequentially.

Figure 19:
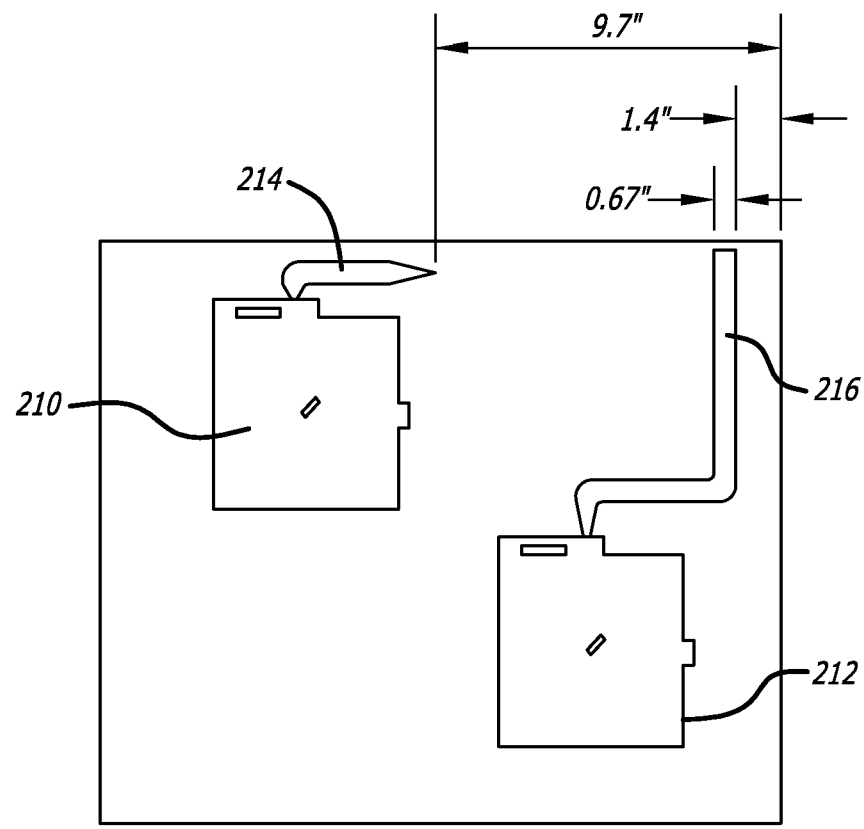
FIG. 19 is a schematic view of the size and placement within the drawer of FIG. 16 of two microstrip or "patch" antennae and their microstrip conductors disposed between respective antennae and the back of the drawer at which they will be connected to SMA connectors in one embodiment, for interconnection with other components.

FIG. 19 is a schematic view of the size and placement within the enclosure 166 of FIG. 16 of two microstrip or "patch" antennae 210 and 212 and their microstrip conductors 214 and 216 disposed between the respective antennae and the back of the enclosure at which they will be connected to SMA connectors (not shown) in one embodiment. Feed lines 58 (FIG. 3) may be connected to those SMA connectors and routed to the computer 44 for use in communicating the RFID signals for further processing. The measurements of the spacing of some of the microstrip components are provided in inches. The spacing of 9.7 in. is equivalent to 24.64 cm. The width of the microstrip line of 0.67 in. is equivalent to 17.0 mm. The spacing of 1.4 in. is equivalent to 3.56 cm. Other configurations and types of receiving antennae may be used, as well as different numbers of such antennae. In the present embodiment, the receiving antennae are mounted on insulation at the bottom inside surface of the metallic enclosure frame 167 so that the receiving patch antennae are not in contact with the metal surfaces of the Faraday cage.

Figure 20:
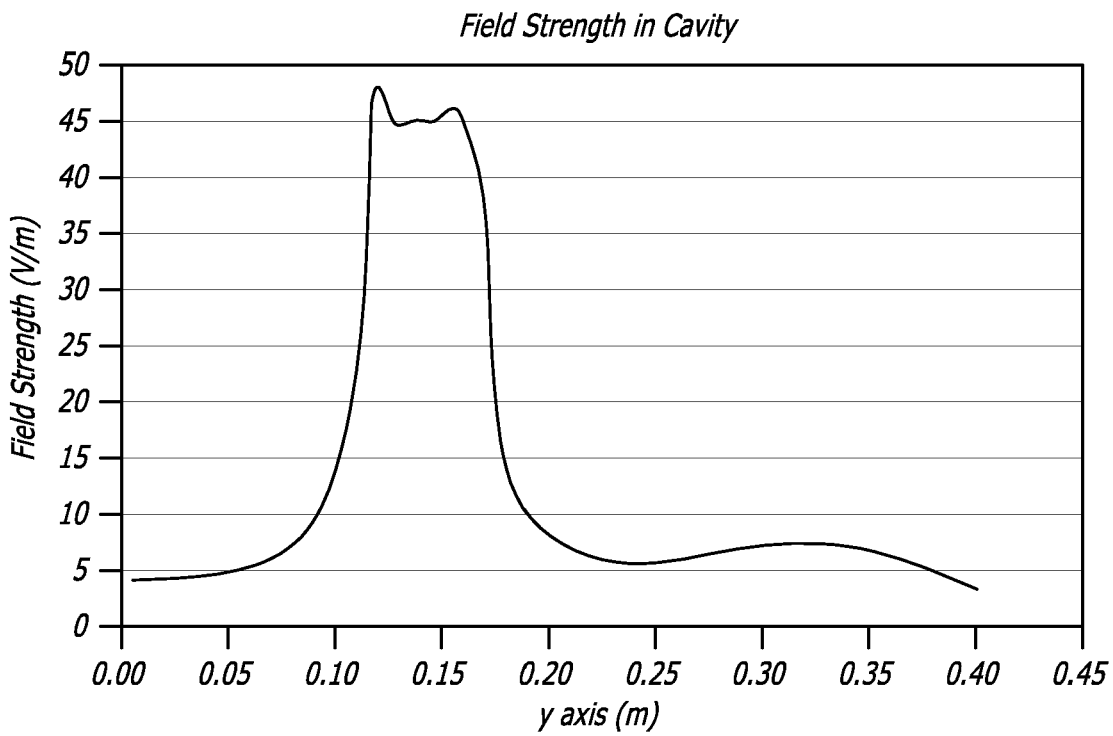
FIG. 20 is diagram of field strength in an embodiment of an enclosure with a probe placed in the enclosure at a position in accordance with the diagram of FIG. 19.
Figure 21:
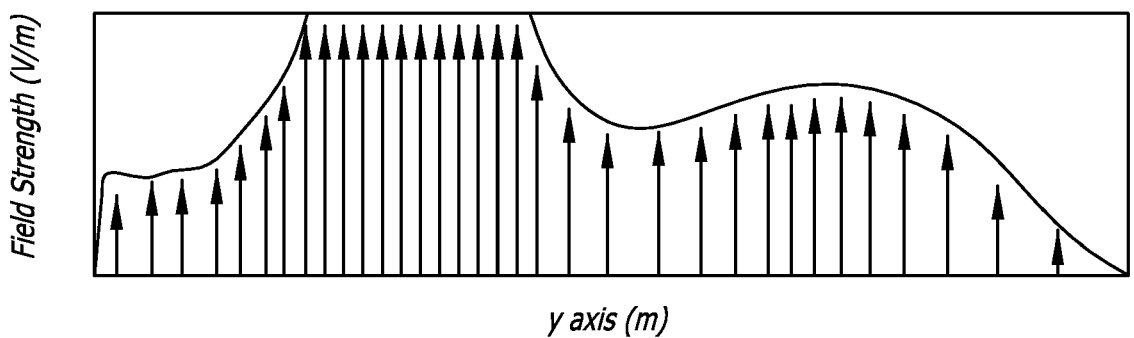
FIG. 21 is a lower scale drawing of the field intensity diagram of FIG. 20 showing a clearer view of the field intensity nearer the front and back walls of the enclosure.

Referring now to FIG. 20, the field intensity or field strength in the enclosure discussed above is shown with the ordinate axis shown in volts/meter and the abscissa axis shown in meters. It will be seen from the diagram that the maximum field intensity occurs at about 5.0 inches (0.127 m) which results from the probe positioned at 5.0 inches (12.7 cm) from the front wall and at a 915 MHz operating frequency. Referring now to FIG. 21, the scale has been reduced although the large rise in field intensity can be seen at 5.0 inches. It can also be more clearly seen that the field intensity falls off at the right wall but remains strong very close to the left wall. Therefore in an embodiment, a second probe was used that was placed 5.0 inches (12.7 cm) from the right wall thereby resulting in a mirror image field intensity to that shown in FIG. 21. The two probes 162 and 164 are activated sequentially and are not both activated simultaneously. It will be noted that better EM field coverage of the enclosure 166 is obtained with the two probes and that RFID tags on articles positioned close to the front wall 161 will be activated by the front probe 162 and that RFID tags on articles positioned close to the rear wall 170 will be activated by the rear probe 164 (see FIG. 13).

Although not intending to be bound by theory, in deriving the probe location for TE modes in a square or rectangular non-resonant cavity, the following equation can be useful:

$$N = 2 \times \frac{L_2 - L_1}{\lambda_g}$$

where: N=positive non-zero integer, for example 1, 2, 3, etc.
$L_1$=distance between probe and back wall
$L_2$=distance between probe and front wall
$\lambda_g$=wavelength in the cavity
$L_1$ cannot be zero for TE modes, which implies that the probe for TE mode excitation cannot be at the front or back wall. For TM modes, the equation is the same, but N can equal zero as well as other positive integers. The probe position cannot be $\lambda_g/2$ from the front or back wall. An $L_1$ and an $L_2$ are chosen such that N can be a positive integer that satisfies the equation. For example, for the enclosure 166 discussed above:

$L_1 = 4.785$ inches $L_2 = 11.225$ inches $\lambda_g = 12.83$ inches

Therefore, $$N = 2 \times \frac{11.215 - 4.785}{12.83} = 1.0$$

The actual enclosure had the probe located at a slightly different location (5.0 inches) than that indicated by the equation (4.785 inches) which was possibly due to the insertion of a plastic drawer in the cavity, which introduces a change in the phase from the reflected signals. The equation above is set up such that the reflected phase from both front and back walls is equal, i.e., they are "in phase" at the probe location.

The wavelength in the enclosure, $\lambda_g$, can be calculated using waveguide equations. Equations for a rectangular cavity are shown below. The cutoff frequency is required for this calculation. The equations will change for a cylindrical cavity or for other shapes.

The cutoff frequency is at the point where g vanishes. Therefore, the cutoff frequency in Hertz is:

$$(f_c)_{mn} = \frac{1}{2\pi\sqrt{\mu\varepsilon}} \sqrt{\left(\frac{m\pi}{a}\right)^2 + \left(\frac{n\pi}{b}\right)^2} \text{ (Hz)}$$

The cutoff wavelength in meters is:

$$(\lambda_c)_{mn} = \frac{2}{\sqrt{\left(\frac{m}{a}\right)^2 + \left(\frac{n}{b}\right)^2}} \text{ (m)}$$

where: a=inside width
b=inside height
m=number of ½-wavelength variations of fields in the "a" direction
n=number of ½-wavelength variations of fields in the "b" direction
$\varepsilon$=permittivity
$\mu$=permeability The mode with the lowest cutoff frequency is called the dominant mode. Since $TE_{10}$ mode is the minimum possible mode that gives nonzero field expressions for rectangular waveguides, it is the dominant mode of a rectangular waveguide with a>b and so the dominant frequency is:

$$(f_c)_{10} = \frac{1}{2a\sqrt{\mu\varepsilon}} \text{ (Hz)}$$

The wave impedance is defined as the ratio of the transverse electric and magnetic fields. Therefore, impedance is:

$$Z_{TE} = \frac{E_x}{H_y} = \frac{jw\mu}{\gamma} = \frac{jw\mu}{j\beta} \Rightarrow Z_{TE} = \frac{k\eta}{\beta}$$

The guide wavelength is defined as the distance between two equal phase planes along the waveguide and it is equal to:

$$\lambda_g = \frac{2\pi}{\beta} > \frac{2\pi}{k} = \lambda$$

where $k_c = \sqrt{\left(\frac{m\pi}{a}\right)^2 + \left(\frac{n\pi}{b}\right)^2}$; and $$\beta = \sqrt{k^2 - k_c^2}$$

Figure 22A:
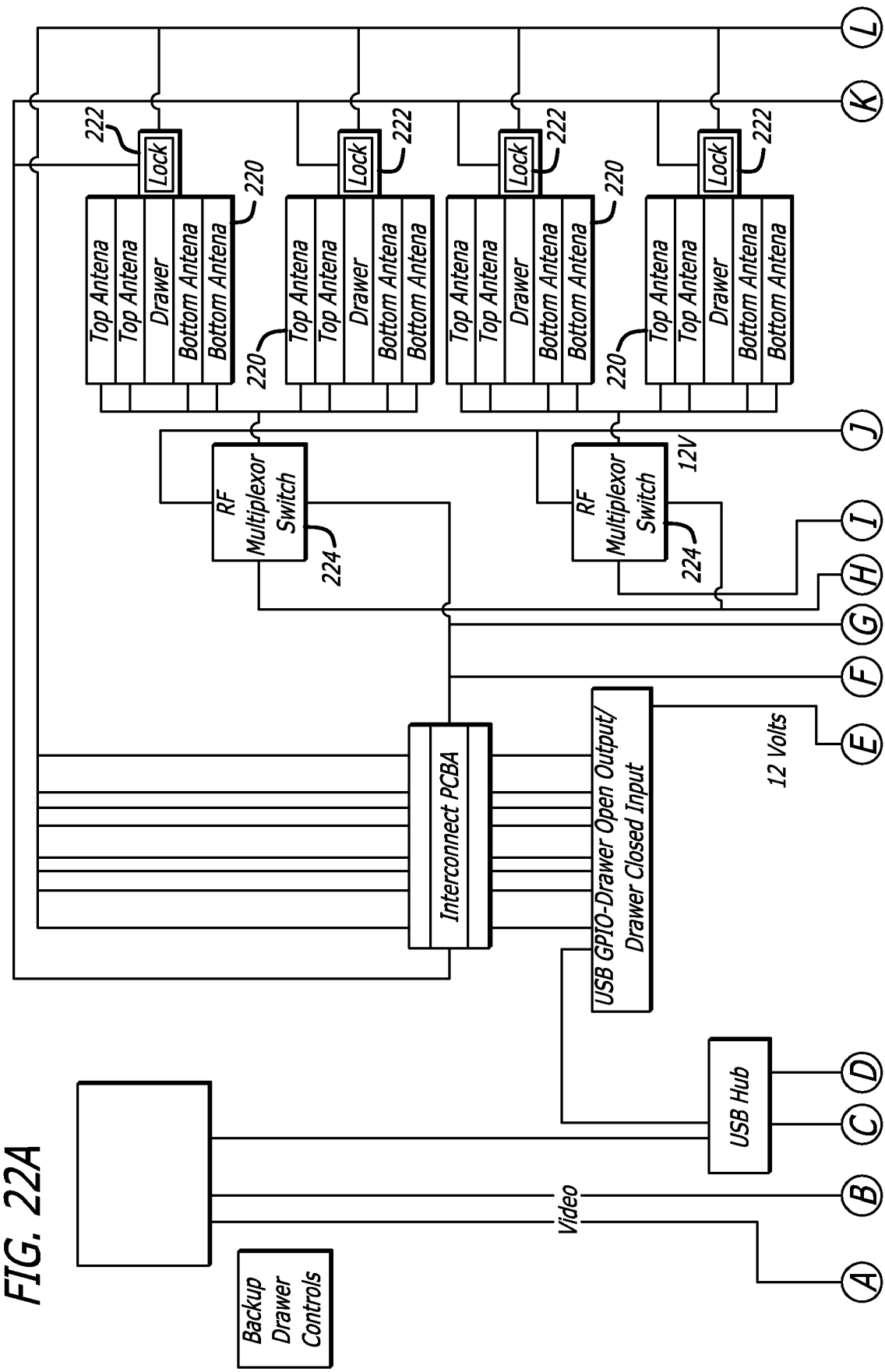
FIGS. 22A and 22B together present a block electrical and signal diagram for a multiple-drawer medical cabinet, such as that shown in FIG. 2, showing the individual multiplexer switches, the single RFID scanner, and power control.
Figure 22B:
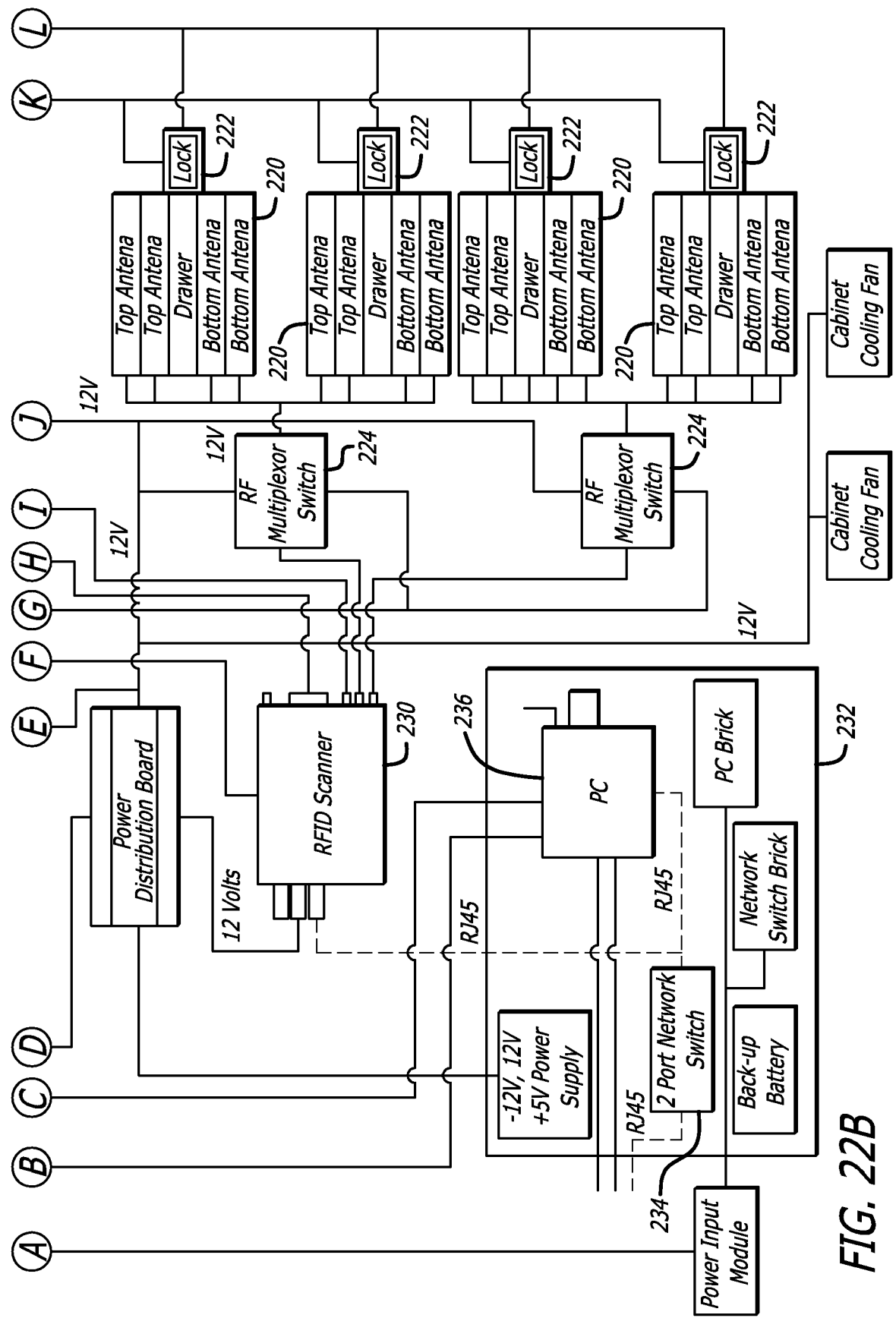

FIGS. 22A and 22B together provide a block electrical and signal diagram for a multiple-drawer medical cabinet, such as that shown in FIG. 2. In this case, the cabinet has eight drawers 220, shown in both FIGS. 22A and 22B. Each drawer includes two top antennae, two bottom antennae and a lock with a lock sensor 222 for securing the drawer. Signals to and from the antennae of each drawer are fed through an RF multiplexer switch 224. Each RF multiplexer switch 224 in this embodiment handles the routing of RF signals for two drawers. RFID activation field and RFID received signals are fed through the respective RF multiplexer switch 224 to a main RFID scanner 230 (see FIG. 22B). The scanner 230 output is directed to a microprocessor 232 (see FIG. 22B) for use in communicating relevant information to remote locations, in this case by wired connection 234 and wireless connection 236 (see FIG. 22B). Various support systems are also shown on FIGS. 22A and 22B, such as power connections, power distribution, back up battery (see FIG. 22B), interconnection PCBA, USB support (see FIG. 22A), cooling (see FIG. 22B), and others.

Figure 23:
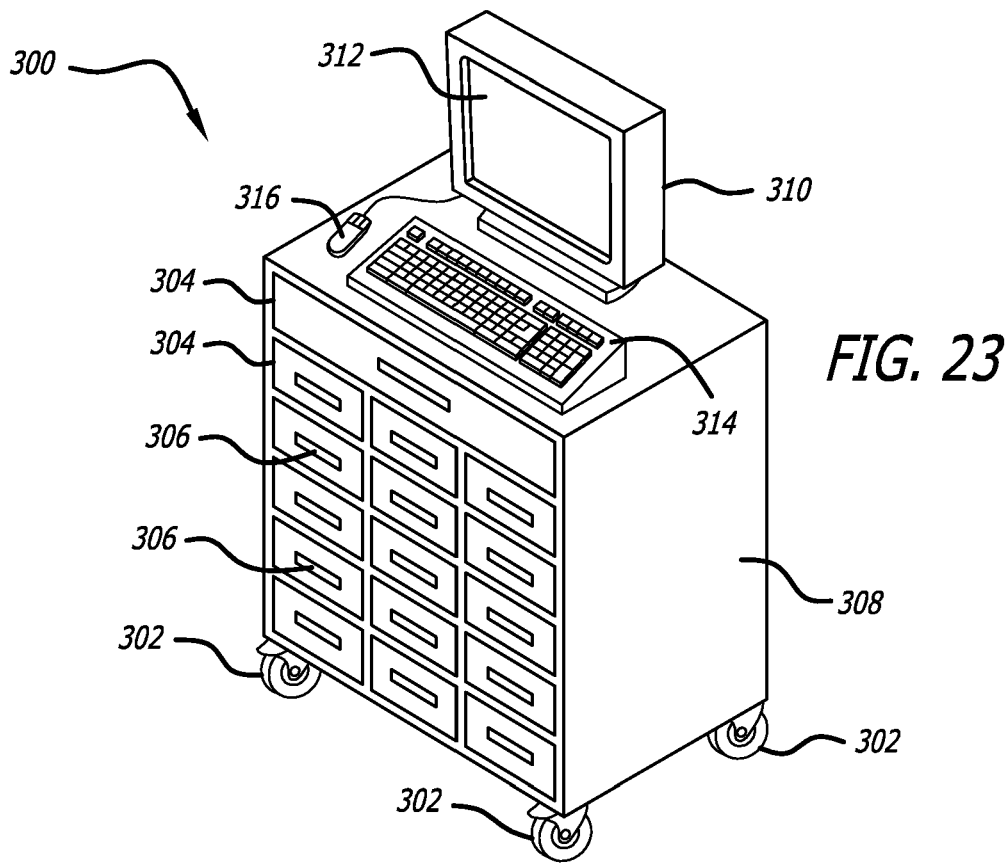
FIG. 23 is a front perspective view of a mobile dispensing cart having a plurality of lockable drawers, each of which may be assigned to a particular patient and contain medical articles to be dispensed to that patient.

Turning now in more detail to FIG. 23, a mobile medication dispensing cart 300 is shown having a plurality of drawers 304, one or more of which is for a particular patient being treated in the area near the cart. Multiple patients may have medications and other medical articles stored in the cart. In this embodiment, the cart 300 also includes a computer 310 with a display 312 and two input devices, one of which is a standard keyboard 314. In this case, the second input device is a biometric sensor/scanner 316 and is used to control access to the drawers 304 of the cart 300. The biometric device reads fingerprints and the computer 310 has, or is connected with a server 360 (discussed below in relation to FIG. 25) that has, access to files that correlate fingerprints to personnel and access levels of those personnel. The computer 310 or remote server determines if the health care provider ("HCP") using the biometric scanner is in the data base as being allowed access to carts and is linked to any patient in the patient data base having a drawer 304 in this particular cart 300. If the HCP meets both requirements, he or she is allowed access to the drawers of the cart. Often mobile dispensing carts have locked drawers for security reasons. However, in a typical cart, the drawers are all locked and unlocked together. It is not possible to choose which to lock and which to unlock. Thus and HCP who gains access to one drawer has access to all drawers and this is where the unfortunate activity of medication "shopping" arises. Such shopping can result in problems where the HCP takes a medication from a drawer that is not the patient's for whom he or she is responsible and the HCP does not notice that the dosage differs. Such shopping activity is curtailed due to aspects of the invention shown herein in embodiments.

According to the particular program used, the HCP may be required to enter into the computer 310 by the keyboard 314 the patient name or code to which the HCP is linked. If that patient has a drawer in the cart, the drawers will be unlocked for the HCP. The relevant drawer can then be opened by pulling its handle 306 and pulling it out of the cart. If the HCP is not linked to any patient having a drawer in the cart, no access will be provided to the HCP. Other input devices may be used to perform the above, including a touch screen that operates both as a display (output device) and an input device.

Figure 24:
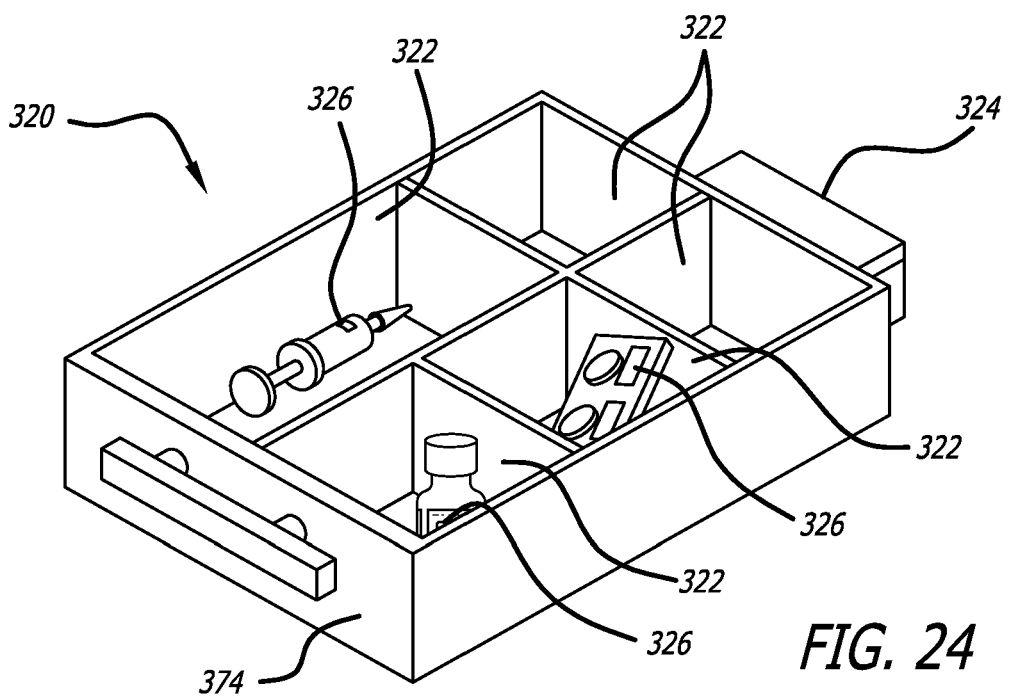
FIG. 24 is a top perspective view of a drawer from the cart of FIG. 23 showing pockets in the drawer for organizing and separating various medical articles to be dispensed to the patient to whom the drawer has been assigned.

Since these mobile dispensing carts 300 are typically not used for emergency medical articles, access to their drawers can be controlled so that management and security of the contents of the cart are improved. Referring now to FIG. 24, the drawer 320 includes a locking feature 324 at the back of the drawer to control access to the drawer. No further details of this locking feature are provided since those of skill in the art are aware of ways to provide a drawer locking system in a cart. However, mechanical and/or electrical controls over access to the drawers can be implemented in such carts. Control over access may be provided by the cart computer 310 or a remote server or other ways.

In accordance with the present embodiment, the mobile cart 300 of FIG. 23 is provided with one or more RFID-enabled enclosures (not shown) in which one or more drawers are located. Embodiments of such RFID enclosures can be seen in FIGS. 13-17. The RFID enclosures shown are configured as Faraday cages and each may contain an RFID exciter/reader. Both are controlled by the local computer 310 in this embodiment and are used to take an inventory of the drawers 304 within the enclosure. As used herein, an RFID reader is a device that not only reads the serial number of a responding RFID tag, but also excites the tag to transmit that serial number. Such RFID-enabled enclosures will enclose more than one drawer and may enclose an entire row of drawers or multiple rows. Due to the size of the enclosure, it is unlikely that only single drawers will be enclosed; however, if equipment should become less bulky and costly, an arrangement where each drawer is separately enclosed may be possible.

One or more drawers 304 of the cart 300 are allocated to a specific patient and are stocked by the pharmacy for twenty-four hours of use, according to hospital practice. In one embodiment, each of the medications or supplies in a specific drawer within the cart is associated with a specific patient via the identification numbers of the RFID tags that are attached to the medications or supplies in the drawer. The pharmacy creates or builds a "patient data base" of the medical articles stocked in the cart for the particular patient and that data base is accessible from the cart. The RFID numbers of the medical articles are associated with that patient and stored in the data base; however, other arrangements for the data base link to the patient are possible. Upon closing a drawer or drawers of the cart, the processor of the computer 310 will run an automated self-inventory of the cart through exciting and reading the RFID tags in the cart. At that time, processor can compare which medical articles remain in the cart and compare them to the lists for the patients to determine if any are missing. Referring to FIG. 24, three medical articles are shown in the pockets 322 of the drawer, each of which has an RFID tag 326 associated with it. In these three cases, the RFID tag is attached to the medical article.

When an HCP identifies himself or herself to the local computer 310 and identifies the patient, access to the drawers 304 of the cart 300 is granted and medications or supplies can be withdrawn. Upon closing the drawer (which will automatically cause it to lock in this embodiment), the local computer performs an automated self-inventory of the RFID-enabled enclosure in which all RFID tags in the cart are read and compared against a data base inventory prior to the door being opened. The system then determines the difference between inventories before this person's access and after this person's access and updates the inventory data base. The medications and/or supplies taken from the cart are noted in the data base and may be scheduled for replacement. This approach provides a higher level of inventory control, accountability, and prevents medication delivery errors.

Figure 25:
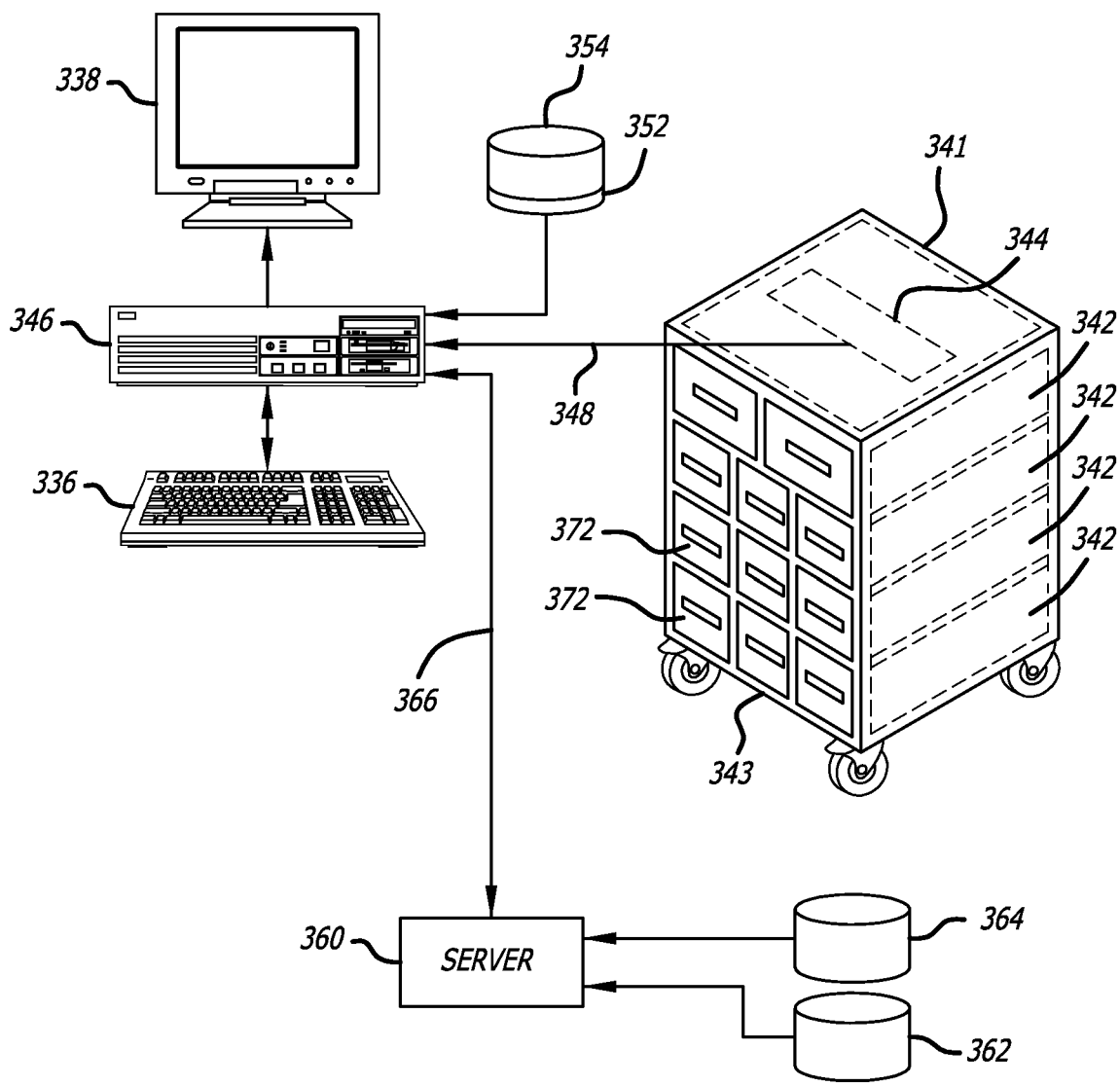
FIG. 25 is a block diagram of a management system for a mobile cart including a computer system, local memory, remote server and remote data bases, the mobile cart having Faraday cages enclosing multiple drawers for reading RFID devices on articles stored in drawers.

FIG. 25 shows an embodiment of a mobile dispensing cart management system 340 according to aspects of the invention. A cart 341 is shown within which are eleven slidable drawers 372 (all drawers are meant to be indicated by numeral 372) in which are stored medical articles for particular patients. The cart 341 also includes four RFID enclosures 342 that comprise Faraday cages within which the multiple drawers are located when the drawers are in the closed configuration. The RFID enclosures have electrically conductive walls and make electrical contact with the front of the drawer which in this embodiment is electrically conductive to provide a six-sided Faraday cage which acts by preventing (or significantly attenuating) electromagnetic energy from entering or escaping the enclosure 342. Each Faraday cage is fitted with an RFID reader 344 configured to interrogate RFID tags located within the respective enclosure. Only one reader is shown in FIG. 25 in dashed lines due to the need to retain clarity in the drawing. The readers 344 are connected to a computer 346 through a connection 348. The connection 348 may be a wired connection, wireless connection, or any other suitable connection for data transfer. In one embodiment, the physical body of the computing system 346 may be mounted to the cart 341, similarly as shown in FIG. 23.

The computing system 346 has a non-volatile memory 354 in which is stored at least one data base ("db") such as the patient data base described above, which may be a local database, or other. The non-volatile memory 354 comprises one or more computer readable media within the computer system 346 and may be located within the computer itself or external to the computer. The memory is shown here as being outside the computer only for clarity of illustration in the discussion and is not meant to limit the invention in any way. In another embodiment, part or all of a relevant database may be stored on a server 360 which may be remote from the cart and from the computer system 346. The computing system 346 connected to the remote server 360 has access to a first remote data base 362 and a second remote data base 364, both connected to the server. As in the local computer, these remote data bases may be stored on a memory that is internal to the server or that is external to the server and may also include a patient data base or a medical article data base or other. Further, the server 360 may be located nearby the local computer 346 or may be remote therefrom. By remote, it is meant that it may be in the same room, or in the same wing, or in the same facility, or may be in the "cloud." The connection 366 to the server 360 may likewise be a wired connection, wireless connection, or any other suitable connection for data transfer. The computer 346 also has a keyboard 336 as an input device and a display 338 as an output device. The display could take the form of a touch screen which would then provide both an input and an output device. The computers shown herein can take different forms. They may be full size desktop computers, laptops, tablets, thin clients, or other.

In one embodiment, the data held on the local data base 352 (on local memory 354) may depend on the location/specialty/facility using the computer system 346. In one embodiment, the remote database 362 at the server 360 may serve as a main database and contain data and formulary for all medical articles for all medical locations/facilities/specialties. The local data base 352 may maintain a copy of the portion of data held on the remote data base 362 that is most relevant to the computer system 346, but can access the remote data base 362 when encountering medical items, medical containers, or other inventory for different facilities/specialties/locations.

The enclosures 342 in FIG. 25 have openings at the front of the cart 341 through which the drawers 372 may be slid into the cart. The drawers are placed completely within the enclosures except for the front of the drawers 374 (see FIG. 24) which in this embodiment close the respective openings and complete the Faraday cage of the enclosure 342. The drawers include a number of medical items shown in FIG. 24 with each article having an RFID tag 326 attached. As discussed previously, each RFID tag has a different stored identification number comprising a few bytes with a check digit. Manufacturers guarantee that each serial number is used only once. Some RFID tags have more complex codes for identifying the RFID tag. The RFID reader 344 will read those identification numbers from the tags, communicate them to the computer 346 which will compare them against one or more data bases either locally 352 or remotely through a server 360 to identify the medical article to which the RFID tag is attached. The process of using the identification numbers of the tags is discussed below.

Figure 26:
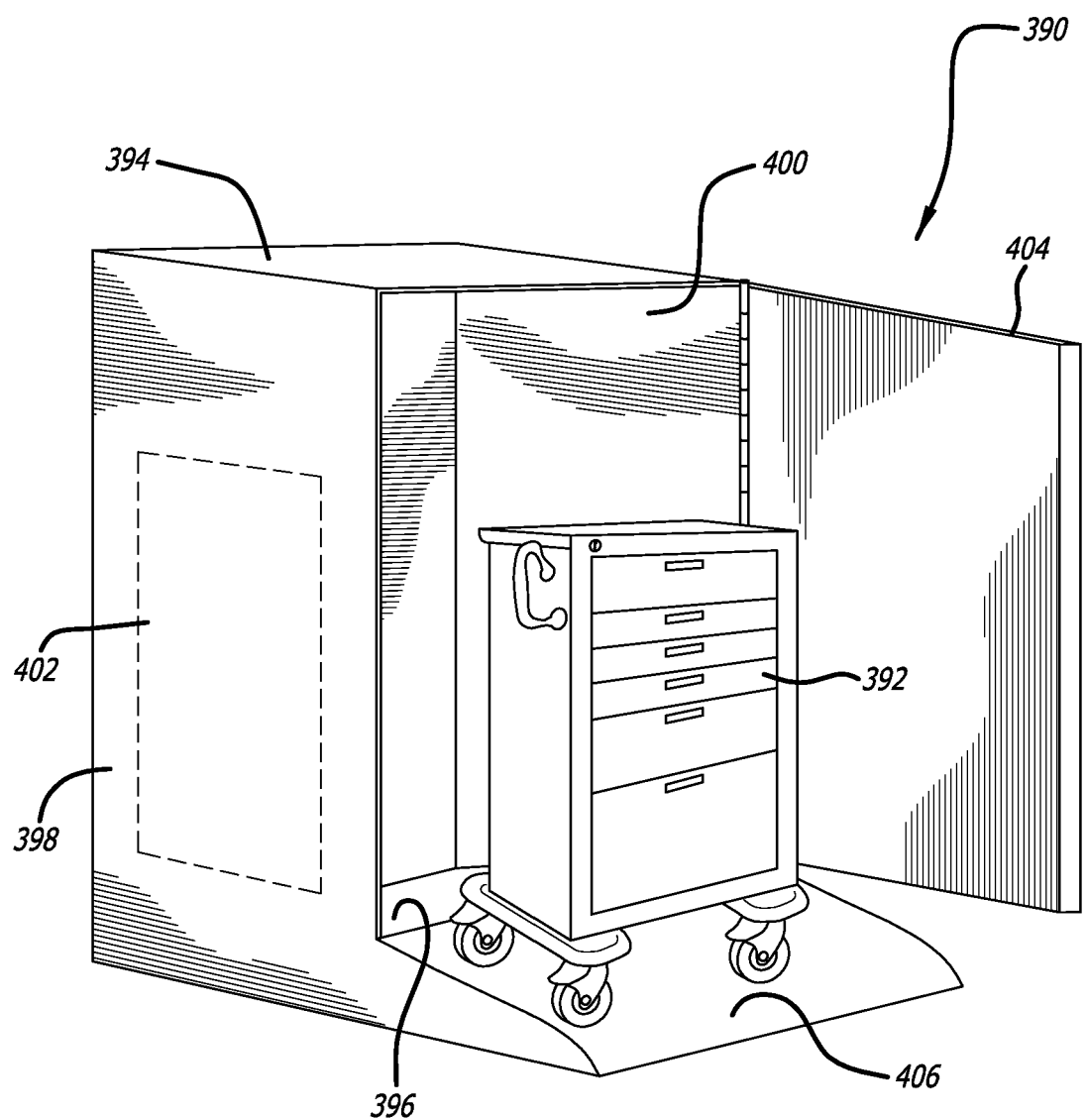
FIG. 26 is a side perspective view of a Faraday cage enclosure for taking the inventory of wireless devices contained in a mobile dispensing cart.

In another aspect in accordance with the invention, in the case where the mobile medication cart does not include an RFID reader, the cart is movable to a location at which an inventory enclosure is located. This may be on the same floor as patient rooms, in the pharmacy, or elsewhere, and is large enough that the entire cart may be pushed into the enclosure. FIG. 26 presents an enclosure 390 of a much larger size so that it can accommodate the entire mobile dispensing cart 392. In this embodiment, enclosure 390 has a ceiling 394 and a floor 396 that are electrically conductive. The enclosure 390 also has two fixed side walls 398 and 400 and a back (not shown) that are electrically conductive. Part of an RFID reader system 402 is shown within the enclosure. The front part 404 of the enclosure is a hinged electrically conductive door that, when closed, completes the Faraday cage of the enclosure 390. Instead of a door, the front 404 may be a flexible panel that is also electrically conductive. Other approaches to providing a covering over the front opening are possible, provided that they complete the Faraday cage about the mobile dispensing cart 392 once it is moved completely within the enclosure 390. In an alternative embodiment, all four sides of the enclosure may be made of flexible panels so that the enclosure can more easily be moved to another location. In one embodiment, the ceiling, floor, sides, back, and front can all be fitted with RFID readers/antennas 402 so that articles within the mobile dispensing cart having RFID tags can be accurately identified.

The enclosure of FIG. 26 includes a ramp 406 that may or may not be attached to the floor 396 of the enclosure 390. The purpose of the ramp is to facilitate rolling the mobile cart into the enclosure. Other means are possible. The RFID exciter/reader 402 is located within the inventory enclosure to excite the RFID tags on the remaining medications and supplies in the mobile cart 392 and read those excited RFID tags. A host computer (not shown) associated with the inventory enclosure or elsewhere will determine the difference between the inventory of remaining medications and supplies in the cart and the inventory taken prior to access given to the drawers. Upon completion of this excitation and reading process, the door 404 is opened and the mobile cart withdrawn. The mobile cart may be resupplied with only the medications or supplies that were removed.

The inventory enclosure 390 may be formed in various ways. A metal frame may be used with flexible electrically conductive material forming the sides so that a door is not necessary. One wall of the flexible electrically-conductive material may be rolled up and the mobile cart pushed into the enclosure. The side may now be rolled down to resume electrical contact with three other sides to complete the Faraday cage. Other means of forming a Faraday cage may be used, including portable materials that may be more easily moved from floor to floor or location to location, assembled, operated, dissembled, and moved again.

It should be noted that use of a Faraday cage is highly beneficial in healthcare facilities due to the ubiquitous presence of medical articles that have RFID tags. Without the ability to electrically isolate the drawer or cart to be inventoried, an RFID reader may inadvertently read the RFID tags of other pharmaceuticals on shelves outside the drawer or cart thereby giving the operator incorrect information that those external read articles are in the drawer or drawers of the cart.

FIG. 27 is a schematic diagram depicting an exemplary implementation of an inventory management system 410 according to an embodiment of the invention. Starting at the top, a data base of medical articles 420 managed by the management system 410 is built. As an example, a medication vial 412 on which an RFID tag 414 is mounted is being registered with the system 410 by entering the RFID tag's serial number 416 along with the relevant information 418 about the medication in the vial 412 into an "articles data base" 420 by the computer 422. In this case, the computer comprises a processor 424, a display 426, and an input device 428 which in this case is a keyboard. An RFID reader 430 obtains the RFID tag's serial number and assigns it to the medication information regarding the medical article to which the RFID tag is mounted. In this case, the information about the medication comprises: the drug name, the dose, the volume, the expiration date, the manufacturer's name, the lot number, the NDC, and the UPC. Other information may also be included. This is then stored in the Articles Data Base or "Articles db" 420. Building the articles data base can be done in different ways and may be automated or may be pre-prepared by the medication manufacturer and given to the healthcare facility in electronic form. The above is repeated for all medications and other medical articles that may be placed in a mobile dispensing cart.

A drawer data base system is shown at the bottom of FIG. 27. In this diagram, the drawers 320 are stocked by the pharmacy patient by patient and the contents of the drawers are read into a patient data base which then links the identity of the patient to the cart and to certain drawers and to the medical articles in the drawers of the cart. This is repeated for all patients whose medical articles are in the cart. The entry of medical article identifiers may be done by reading their RFID tags or by other means.

Figure 28:
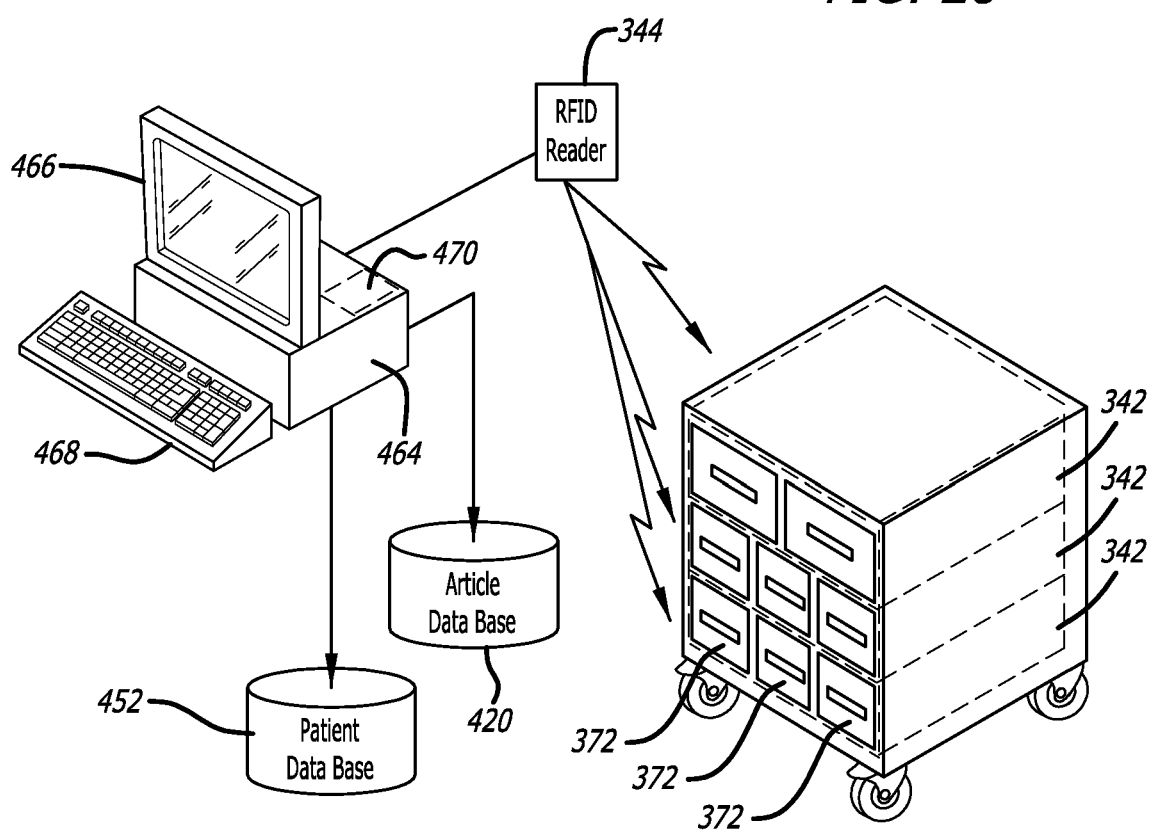
FIG. 28 is a schematic block diagram of a computer program that provides a method for managing access to and inventory of a mobile dispensing cart in which articles removed from the cart are checked against a data base for a patient and if the article removed was not stored in the cart for the particular patient, an alarm is given.

Referring now to FIG. 28, a block diagram shows monitoring of the cart as access is obtained and medical articles are removed. The RFID reader 344 is shown removed from the Faraday enclosures 342 and the drawers 372 but this is for convenience of illustration only. In summary when a drawer or drawers 372 are closed, a program is run by the computer 464, the program stored in the computer's memory 470 or elsewhere, to manage the contents of the cart. Each of the enclosures 342 will read the contents of the drawers in the enclosure and report the RFID serial numbers received by the reader 344. The computer will compare those RFID serial numbers to the patient data base 452 and note any articles missing. The computer stores such data for possible future reference.

Figure 29:
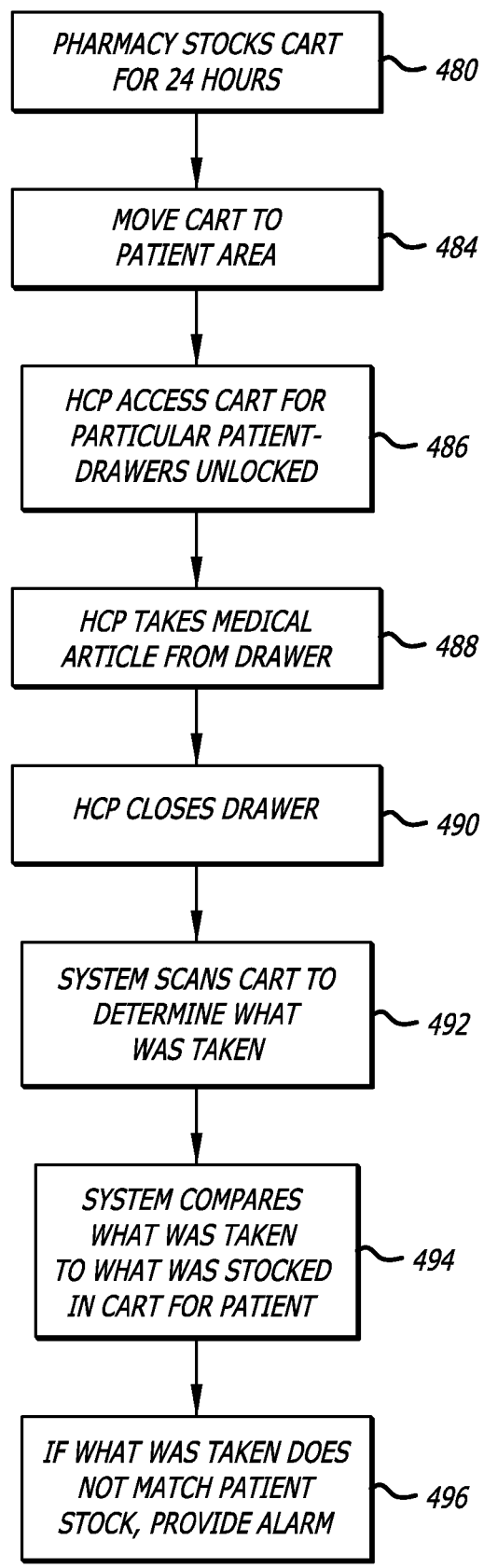
FIG. 29 is a flow chart of managing access to a mobile cart and monitoring the removal of articles from the cart to assure that they are removed for the correct patient.

Referring now to FIG. 29, a flow chart is provided that describes an embodiment of a method of managing the inventory of a mobile dispensing cart in accordance with aspects of the invention. The cart is stocked by the pharmacy 480 with medical articles needed by patients in a certain area of the facility for twenty-four hours. The cart is then moved 484 to the area of the patients, which may be in the patients' room, in a hallway, or elsewhere. An HCP desires to take a medical article from the cart to dispense that article to a particular patient. The HCP obtains access to the cart by identifying the HCP and the patient. The cart will then unlock all drawers providing access to the medical articles stored in the cart.

The HCP removes a medical article 488 and closes the drawer 490. At that time, the program that is managing and monitoring the cart inventory scans all the drawers to determine if anything was taken and if so, what was taken 492. If the program determines that a medical article was taken, it then compares that medical article to the data base of medical articles in the cart to determine if what was taken was a medical article of the patient, for whom access to the cart was allowed. If the program does not find a match of the taken article to the patient's data base, the program will provide an alarm 496. This alarm will mean that the HCP has taken a medical article stocked in the cabinet for a different patient. The alarm may be provided locally and may also be communicated elsewhere as arranged. If the removal of the incorrect article was inadvertent, the alarm will prompt the HCP to return the article to the cart and search more carefully for the correct article for the patient.

Figure 30:
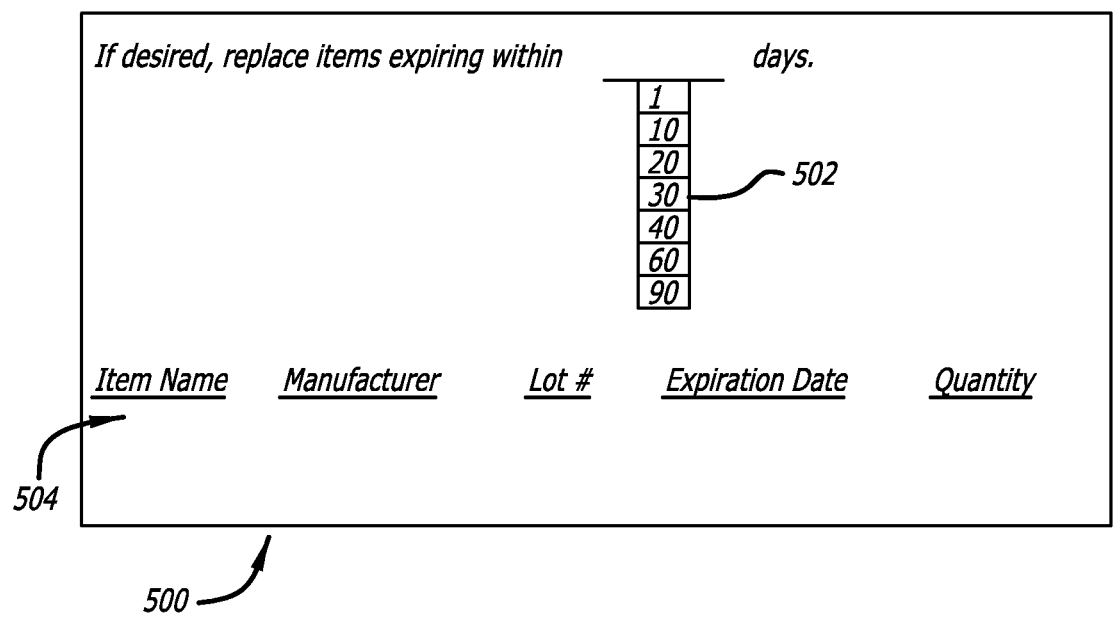
FIG. 30 is a screen shot of a program by which the expiration dates of medical articles in a mobile dispensing cart can be checked.

Not only does this system manage the cart to avoid incorrect dispensing, it may also provide an HCP with a means to monitor the cart inventory for expired or recalled medical articles. The HCP may ask the cabinet to scan all medical articles for expiration dates. This may involve matching the RFID serial numbers to article information in the medical article data base (FIG. 27, upper portion of figure) to obtain the exact expiration date. The program would then ask the HCP what expiration period the HCP wants to search. A screen shot in FIG. 30 includes a drop-down list from which such expiration periods may be selected (for example, 1 day, 10 days, etc.) A period is selected and the program compares all expirations dates against that term. If any match, they are listed in the section 504 below the drop-down box.

The program next proceeds to determining if any scanned medical articles have been recalled by the manufacturer, or the FDA, or otherwise. The comparison of the identification of the detected medical articles in the tray are compared to a "Recalled" data base (not shown) and if any articles match recalled articles, it is then determined if a substitute medical article exists. If none exists, an alarm is provided. If a substitute article does exist, a substitute is located and may be supplied to the drawer. If no recalled articles exist in the drawer, the program indicates such status.

Multiple data bases may be employed in the system and method described above. According to one embodiment, the system 340 (FIG. 25) and the method 489 (FIG. 29) may search one or more data bases of medical article information matching the identification data. In one embodiment the identification data may be found in multiple data bases each data base containing different information. As by way of example and not limitation, the name, dosage, lot code and expiration date may be on one data base while recall status may be in another data base. In another embodiment all the medical item information may be held in one data base which may have its information on other data bases as backup. In yet another embodiment, medical item information may be stored on a local data base within the computing device connected to the enclosure, and the local data base may be updated periodically over a network connection from one or more remote data bases.

Any alarms that are provided may be done so visually, such as by displayed on a computer screen, audibly, such as through speaker sounds, and/or tactile by vibrations. Other means or combinations of means for communicating an alarm condition may be used.

The invention will provide a means for more control over inventory allocated to a specific patient. The invention will prevent "shopping" for medications to fulfill a patient's orders. The ability to include Faraday cages and enclosures in which robust EM fields are produced when the enclosure is of a size much smaller than a resonant cavity for the frequency of operation of the RFID devices results in a large improvement in the art. In one case, a 27 cubic feet enclosure is needed for a resonant cavity at the frequency of operation. In accordance with aspects of the invention, a robust EM field similar to that of the resonant cavity was produced in a 1.4 cubic feet enclosure at the same frequency thus resulting in a tremendous advantage in exciting and reading RFID tags in small enclosures.

According to one embodiment, the data files within the databases containing medical information may take the form of a comma separated value list which may have multiple data fields and may look like "Name, Dosage, and Expiration." Other serialized formats may be used to contain the data, including but not limited to, Extensible Markup Language (XML), JavaScript Object Notation (JSON), etc. The data may also take the form of proprietary file formats created by medical article manufacturers. Furthermore, the data may contain a pointer or addresses to additional data providing additional information about the medical item or medical container. On example of additional information may be a data representation of a medical item's image. There are many different file or data formats that may be used to store medical information and any suitable format is contemplated within this invention. In one embodiment, multiple datasets using different data formats containing medical item information may be used, each for a particular medical item manufacturer or distributor. A system may be configured to identify particular datasets based on the identification data from a data carrier (such as an RFID tag). In an alternative embodiment, a single data format may be used across all medical items independent of manufacturers.

In one embodiment, an inventory management system and method in accordance with the invention may use color indicators to communicate any differences/anomalies with the articles within the medical container and the inventory list. The inventory management system and method may also provide expiration indicators. As an example, but not by way of limitation, expiration indicators may include displaying a countdown of the number of days left until expiration of a medical article. In another embodiment, a color indicator using color gradients or color coding may indicate the life of the medical article such as green to red, white to black, etc. Each end of the color/gradient spectrum may represent the life or expiration of a medical article.

Displays may use multiple windows. Each window may display different information regarding the contents of the scanned medical container such as a window for missing articles, a window for expired articles, a window for incorrect or additional articles not part of the container's inventory, a window for an inventory list, a window for recalled articles, and a window for aggregated information. Each window may have an image display, name, dosage, number of articles, and expiration or recall status indicator. Each window may also have a scroll bar for additional data that does not fit in a single window. In an alternative embodiment, a single window may be used and the user may be provided with the ability to select what is displayed in the window.

The computers 310, 346, 422, and 464 across the figures may take any suitable form, including but not limited to, an embedded computer system, a system-on-chip (SOC), a single-board computer system (SBC) (such as, for example, a computer-on-module (COM) or system-on-module (SOM)), a laptop or notebook computer system, a smart phone, a personal digital assistant (PDA), a server, a tablet computer system, a kiosk, a terminal, a mainframe, a mesh of computer systems, etc. The computers may be a combination of multiple forms. The computers may include one or more computer systems, be unitary or distributed, span multiple locations, span multiple systems, or reside in a cloud (which may include one or more cloud components in one or more networks).

In one embodiment, the computers may include one or more processors, memory, storage, an input/output (I/O) interface, a communication interface, and a bus. Although this disclosure describes and illustrates a particular computer system having a particular number of particular components in a particular arrangement, this disclosure contemplates other forms of computer systems having any suitable number of components in any suitable arrangement.

In one embodiment, a processor includes hardware for executing instructions, such as those making up software. Herein, reference to software may encompass one or more applications, byte code, one or more computer programs, one or more executable, one or more instructions, logic, machine code, one or more scripts, or source code, and vice versa, where appropriate. As an example and not by way of limitation, to execute instructions, a processor may retrieve the instructions from an internal register, an internal cache, memory or storage; decode an execute them; and then write one or more results to an internal register, an internal cache, memory, or storage. In one embodiment, a processor may include one or more internal caches for data, instructions, or addresses. Memory may be random access memory (RAM), static RAM, dynamic RAM or any other suitable memory. Storage maybe a hard drive, a floppy disk drive, flash memory, an optical disk, magnetic tape, or any other form of storage device that can store data (including instructions for execution by a processor).

In one embodiment, storage may be mass storage for data or instructions which may include, but not limited to, a HDD, solid state drive, disk drive, flash memory, optical disc (such as a DVD, CD, Blu-ray, and the like), magneto optical disc, magnetic tape, or any other hardware device which stores may store computer readable media, data and/or combinations thereof. Storage may be internal or external to computer system.

In one embodiment, an input/output (I/O) interface includes hardware, software, or both for providing one or more interfaces for communication between a computer system and one or more I/O devices. Computer systems may have one or more of these I/O devices, where appropriate. As an example but not by way of limitation, an I/O device may include one or more mouses, keyboards, keypads, cameras, microphones, monitors, display, printers, scanners, speakers, cameras, touch screens, trackball, trackpad, biometric input device or sensor, or the like.

In still another embodiment, a communication interface includes hardware, software, or both providing one or more interfaces for communication between one or more computer systems or one or more networks. A communication interface may include a network interface controller (NIC) or a network adapter for communicating with an Ethernet or other wired-based network or a wireless NIC or wireless adapter for communications with a wireless network, such as a local wireless network. In one embodiment, a bus includes any hardware, software, or both coupling components of a computer system to each other.

"Medical article" is used in this document its broadest sense. For example, a medical article can be a medical device, a pharmaceutical drug, a lab specimen, a blood product, a human organ, a hospital scrub, a surgical instrument, a medical implant, a sponge or gauze pad, a healthcare institution code tray containing drugs to be tracked, and a code tray containing medical devices to be tracked.

As has been described, the various embodiments of the present invention relates to a system and method for medical article inventory and management. For purposes of explanation, specific nomenclature is set forth to provide a thorough understanding of the present invention. Description of specific applications and methods are provided only as examples. Various modifications to the embodiments will be readily apparent to those skilled in the art and the general principles defined herein may be applied to other embodiments and applications without departing from the spirit and scope of the invention. Thus the present invention is not intended to be limited to the embodiments shown, but is to be accorded the widest scope consistent with the principles and steps disclosed herein.

Although RFID tags are used herein as an embodiment, other data carriers that communicate through electromagnetic energy may also be usable.

While the invention has been described in connection with what is presently considered to be the most practical and preferred embodiments, it is to be understood that the invention is not to be limited to the disclosed embodiments and elements, but, to the contrary, is intended to cover various modifications, combinations of features, equivalent arrangements, and equivalent elements included within the spirit and scope of the appended claims.

Unless the context requires otherwise, throughout the specification and claims that follow, the word "comprise" and variations thereof, such as, "comprises" and "comprising" are to be construed in an open, inclusive sense, which is as "including, but not limited to."

While particular embodiments of the present invention have been described, it is understood that various different modifications within the scope and spirit of the invention are possible. The invention is limited only by the scope of the appended claims.

What is claimed is:

1. An inventory management system for surrounding and electrically isolating a medical tray containing medical articles to be tracked, each of the medical articles contained by the tray having an attached wireless data carrier that is responsive to electrical energy of a certain frequency range to transmit identification data that is indicative of the identity of the wireless data carrier, the inventory management system comprising:
- an inventory enclosure comprising assemblable and disassemblable walls, the sizes of the walls selected so that when assembled, an interior space is created within the walls that is large enough to receive a medical tray to be inventoried, the walls being formed of electrically conductive material and electrically interconnected with other walls to electrically isolate a medical tray located into the interior space, wherein the walls are configured to result in the inventory enclosure being easily assembled, disassembled, moved, and reassembled in another location;
- wherein the walls of the inventory enclosure are configured to provide an opening to the interior space which allows for moving a medical tray into the interior space for inventorying and allows for the tray to be moved out of the interior space, and when the opening is closed, the plurality of walls electrically isolate the tray located in the interior space;
- a data carrier reader disposed within the interior space and configured to transmit interrogating electrical energy to data carriers located on medical articles in a tray that is located within the interior space and to receive responsive identification data signals from data carriers, the reader also configured to communicate inventory data signals containing the data transmitted by the data carriers in the responsive identification data signals;
- a non-volatile memory in which is stored a medical article data base, the medical article data base comprising information that links a data carrier to a medical article to which it is attached including identification of the medical article, the non-volatile memory further comprising a tray inventory data base, the tray inventory data base including a list of medical articles assigned to be located in a tray; and
- a host computer having a communication interface that receives the inventory data signals from the reader, the host computer being programmed to compare the received inventory data signals to the medical article data base to determine information about medical articles to which data carriers are attached in the tray that is being inventoried.

2. The inventory management system of claim 1 wherein:
the non-volatile memory additionally stores a list of medical articles assigned to a tray;
wherein the host computer is further programmed to compare the received inventory data signals from the reader, compare them to the stored tray inventory list, and indicate differences between the inventory indicated as actually being in the tray by the received inventory data signals and the stored inventory list.

3. The inventory management system of claim 1 wherein:
the host computer also being programmed to store a present inventory of a tray that is being inventoried within the inventory enclosure, compare the present inventory of the tray to a previous inventory of the same tray that is stored in the tray inventory data base, and indicate any difference between the present inventory and the previous inventory.

4. The inventory management system of claim 1 wherein the walls of the enclosure comprise a floor, a ceiling, and a plurality of side walls, and wherein the side walls are flexible panels whereby the enclosure can be more easily moved to another location.

5. The inventory management system of claim 1 wherein the inventory enclosure comprises flexible electrically conductive material forming the walls wherein at least one of the flexible electrically-conductive material walls may be rolled up to admit a tray to the interior space for inventorying.

6. The inventory management system of claim 1 wherein one of the plurality of walls comprises a floor panel and further comprising a ramp placed at the floor panel to facilitate movement of the tray into and out of the interior space of the enclosure.

7. The inventory management system of claim 1:
wherein the data carriers comprise radio frequency identification (RFID) tags; and
wherein the walls comprise a ceiling, a floor, side walls, a back wall, and a front wall, all of which are fitted with an RFID reader;
whereby the RFID tags on medical articles within the tray being inventoried in the interior space are more likely to be accurately identified.

8. The inventory management system of claim 1 wherein the non-volatile memory comprises a data base of wireless data carrier identifications linked to medical article data in which one of those medical article data is an expiration date of the respective medical article;
wherein the host computer is further programmed to receive the data carrier identification data, access the data base of medical article data corresponding to that data carrier identification and compare the expiration date of the identified medical articles to a selected date; and
wherein the host computer being further programmed to provide a notice if the expiration date of a medical article falls on or before the selected date.

9. The inventory management system of claim 1 wherein the non-volatile memory includes a recalled data base in which data pertaining to recalled articles are stored; and
wherein the host computer further being programmed to compare the identification data of the medical articles in the tray to the recalled article data base in the memory and if the comparison shows that a medical article is recalled, to provide a notice of such recall status.

10. The inventory management system of claim 9 wherein the host computer is further programmed to access the recalled data base to determine if a substitute medical article exists for any medical articles in the tray that have shown to be recalled.

11. The inventory management system of claim 10 wherein the host computer is further programmed to provide an alarm if no substitute medical article is found in the recalled medical data base for any article shown to be recalled.

12. The inventory management system of claim 9 wherein the recalled data base is stored as a separate data base on the non-volatile memory.

13. The inventory management system of claim 1 further comprising a visual display device;
wherein the non-volatile memory stores a medical article data base that includes data concerning medical articles that are stored in the tray; and
wherein the host computer is further programmed to:
control the display device to display a drop-down list of a plurality of selectable periods having varying time periods before an expiration date;
receive a selection of one of the selectable periods before an expiration date;

read the data carriers attached to the medical articles in the tray;

access the non-volatile memory to locate an expiration date from the medical article data base for each of the medical articles located and read in the tray;

compare expiration dates of the located and read medical articles in the tray to the selected expiration period, and provide a notice of the located articles' expiration within the selected expiration period if any of the located and read medical articles in the tray have expiration dates that fall in the selected expiration period.

14. The inventory management system of claim 1 wherein the medical articles of the tray have been assigned to certain patients, the host computer being further programmed to:

create in a non-volatile memory a stored medical articles data base of all medical articles in the tray and the names of the patients to whom the medical articles in the tray are to be administered; and compare a medical article determined to have been taken from the tray to the data base stored on the non-volatile memory of all medical articles in the mobile dispensing cart to determine if the medical article taken was to be administered to the correct patient.

15. A method of managing an inventory of a medical tray containing medical articles to be tracked, each of the medical articles contained by the tray having an attached wireless data carrier that is responsive to electrical energy of a certain frequency range to transmit identification data that is indicative of the identity of the wireless data carrier, the method of managing an inventory:

surrounding and electrically isolating a medical tray with an inventory enclosure comprising assemblable and disassemblable walls, the sizes of the walls selected so that when assembled, an interior space is created within the walls that is large enough to receive a medical tray to be inventoried, the walls being formed of electrically conductive material and electrically interconnected with other walls to electrically isolate a medical tray located into the interior space, wherein the walls are configured to result in the inventory enclosure being easily assembled, disassembled, moved, and reassembled in another location;

wherein the walls of the inventory enclosure are configured to provide an opening to the interior space which allows for moving a medical tray into the interior space for inventorying and allows for the tray to be moved out of the interior space, and when the opening is closed, the plurality of walls electrically isolate the tray located in the interior space;

reading data carriers attached to medical articles contained in a medical tray that is disposed within the interior space by transmitting interrogating electrical energy into the interior space and receiving responsive identification data signals from data carriers;

communicating the inventory data signals containing the data transmitted by the data carriers in the responsive identification data signals;

storing in a non-volatile memory a medical article data base, the medical article data base comprising information that links a data carrier to a medical article to which it is attached including identification of the medical article, the non-volatile memory further comprising a tray inventory data base, the tray inventory data base including a list of medical articles assigned to be located in a tray; and receiving the inventory data signals by a communication interface of a host computer and comparing the received inventory data signals to the medical article data base to determine information about medical articles to which data carriers are attached in the tray that is being inventoried.

16. The method of managing an inventory of claim 15 comprising:

storing a list of medical articles assigned to a tray in the non-volatile memory;

comparing the received inventory data signals from the reader to the stored tray inventory list; and indicating differences between the inventory indicated as actually being in the tray by the received inventory data signals and the stored inventory list.

17. The method of managing an inventory of claim 15 comprising:

storing a present inventory of a tray that is being inventoried within the inventory enclosure;

comparing the present inventory of the tray to a previous inventory of the same tray that is stored in the tray inventory data base, and indicating any difference between the present inventory and the previous inventory.

18. The method of managing an inventory of claim 15 comprising rolling up flexible electrically conductive material forming a wall of the inventory enclosure to admit a tray to the interior space for inventorying.

19. The method of managing an inventory of claim 15, wherein the step of reading data carriers attached to medical articles contained in a medical tray that is disposed within the interior space comprises transmitting interrogating electrical energy into the interior space and receiving responsive identification data signals from data carriers by radio frequency identification (RFID) tag readers located within the interior space.

20. The method of managing an inventory of claim 15, further comprising:

receiving the data carrier identification data;

comparing data carrier identification data to a data base of wireless data carrier identifications linked to medical article data in which one of those medical article data is an expiration date of the respective medical article;

receiving access to a data base of medical article data corresponding to that data carrier identification and comparing the expiration date of the identified medical articles to a selected date; and providing a notice if the expiration date of a medical article falls on or before the selected date.

21. The method of managing an inventory of claim 15, comprising comparing the identification data of the medical articles in the tray to a recalled article data base in the non-volatile memory and if the comparison shows that a medical article is recalled, providing a notice of such recall status.

22. The method of managing an inventory of claim 21, further comprising accessing the recalled data base to determine if a substitute medical article exists for any medical articles in the tray that have shown to be recalled.

23. The method of managing an inventory of claim 22, further comprising providing an alarm if no substitute medical article is found in the recalled medical data base for any article shown to be recalled.

24. The method of managing an inventory of claim 15, further comprising:

storing a medical article data base that includes data concerning medical articles that are stored in the tray;

controlling a display device to display a drop-down list of a plurality of selectable periods having varying time periods before an expiration date;

receiving a selection of one of the selectable periods before an expiration date;

reading the data carriers attached to the medical articles in the tray;

accessing the non-volatile memory to locate an expiration date from the medical article data base for each of the medical articles located and read in the tray;

comparing expiration dates of the located and read medical articles in the tray to the selected expiration period, and providing a notice of the located articles' expiration within the selected expiration period if any of the located and read medical articles in the tray have expiration dates that fall in the selected expiration period.

25. The method of managing an inventory of claim 15, further comprising:

storing in a non-volatile memory a medical articles data base of all medical articles in the tray and the names of the patients to whom the medical articles in the tray are to be administered; and comparing a medical article determined to have been taken from the tray to the data base stored on the non-volatile memory of all medical articles in the mobile dispensing cart to determine if the medical article taken was to be administered to the correct patient.

\* \* \* \* \*